United States Patent
Safe et al.

(10) Patent No.: US 7,812,003 B2
(45) Date of Patent: Oct. 12, 2010

(54) ANTISENSE MICRORNA AND USES THEREFOR

(76) Inventors: Stephen H. Safe, 4307 Spring Hill Dr., College Station, TX (US) 77845; Sudhakar Chintharlapalli, 2250 Holly Hall, Apt. 237, Houston, TX (US) 77054; Susanne U. Talcott, 15801 Flagstone Ct., College Station, TX (US) 77845

(*) Notice: Subject to any disclaimer, the term of this patent is extended or adjusted under 35 U.S.C. 154(b) by 0 days.

(21) Appl. No.: 12/221,266

(22) Filed: Aug. 1, 2008

(65) Prior Publication Data

US 2009/0099123 A1      Apr. 16, 2009

Related U.S. Application Data

(60) Provisional application No. 60/962,996, filed on Aug. 2, 2007.

(51) Int. Cl.
*A61K 48/00* (2006.01)
*C07H 21/02* (2006.01)
*C07H 21/04* (2006.01)

(52) U.S. Cl. .................. 514/44; 536/23.1; 536/24.3; 536/24.33; 536/24.5

(58) Field of Classification Search .............. None
See application file for complete search history.

(56) References Cited

U.S. PATENT DOCUMENTS 5,801,154 A * 9/1998 Baracchini et al. ......... 514/44 A
2008/0050744 A1* 2/2008 Brown et al. .................. 435/6

OTHER PUBLICATIONS

Scott et al., Rapid Alteration of MicroRNA Levels by Histone Deacetylase Inhibition, 2006, Cancer Res, 66(3), pp. 1277-1281.*

* cited by examiner

*Primary Examiner*—Amy Bowman
(74) *Attorney, Agent, or Firm*—Benjamin Aaron Adler

(57) ABSTRACT

Provided herein are methods to suppress specificity protein (Sp) activity in a cell associated with a cell proliferative disease. The methods are effective to inhibit a microRNA in the cell using an antisense microRNA oligonucleotide which results in an increase in expression of a specificity protein (Sp) suppressor gene thereby inducing Sp degradation, apoptosis or growth arrest by releasing inhibitors of G2/M (Myt-1) or inhibition. Also provided are methods of treating a cancer using the antisense microRNA oligonucleotide. In addition the present invention provides antisense microRNA-27a oligonucleotides useful in the methods described herein.

17 Claims, 26 Drawing Sheets

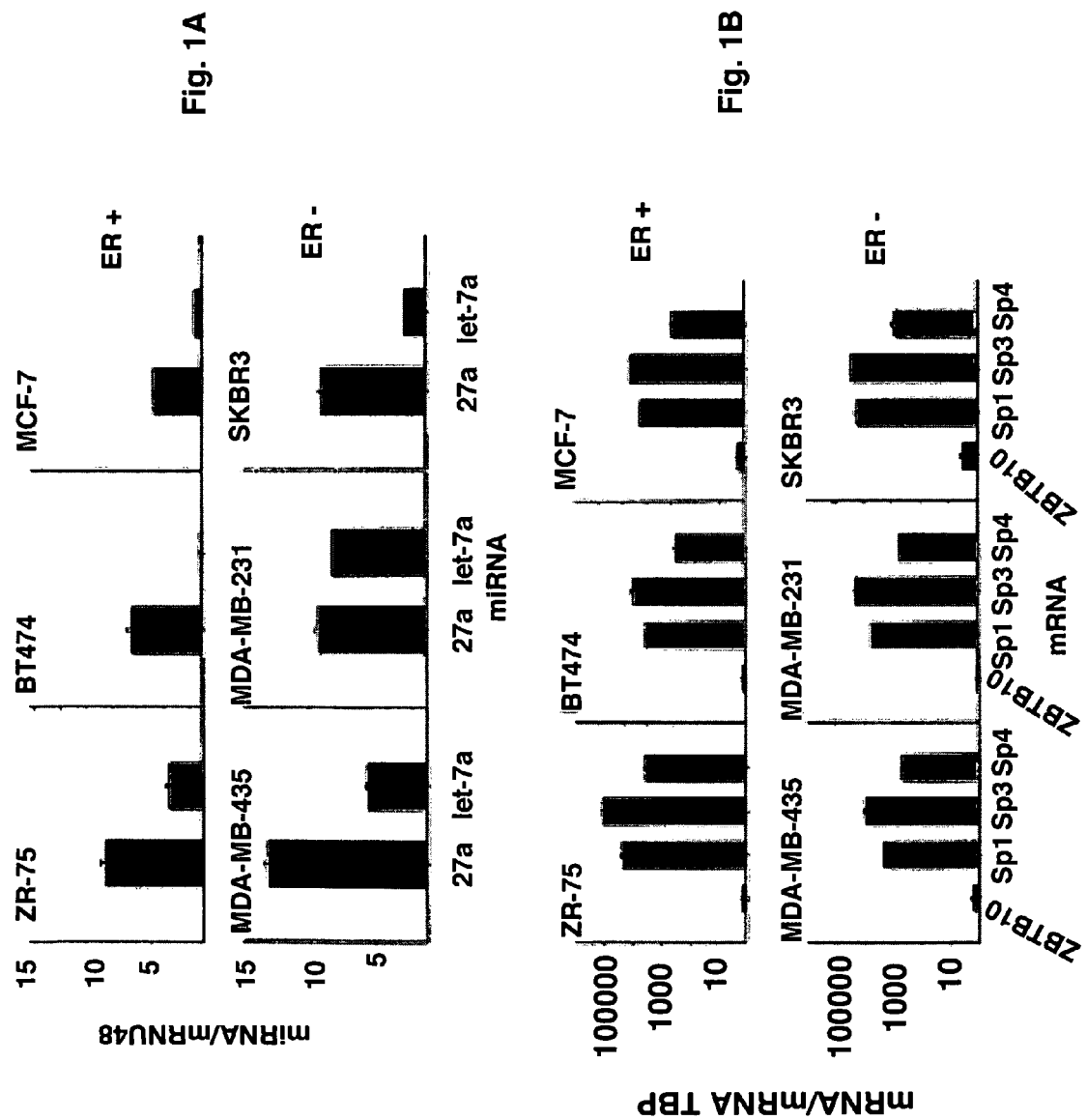

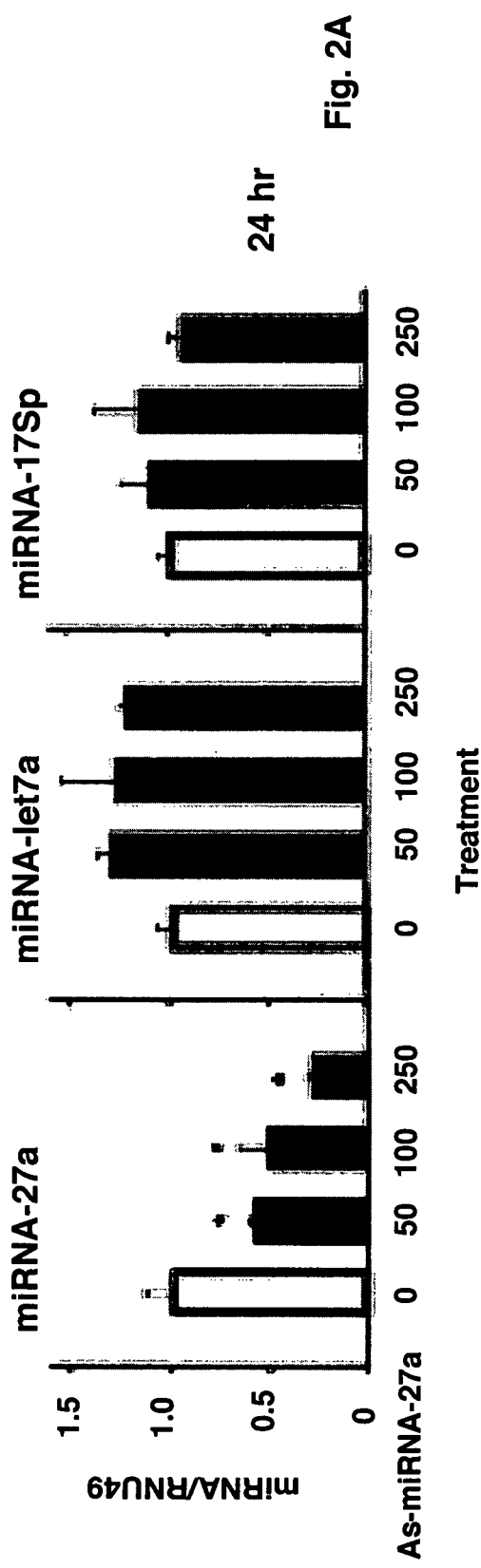
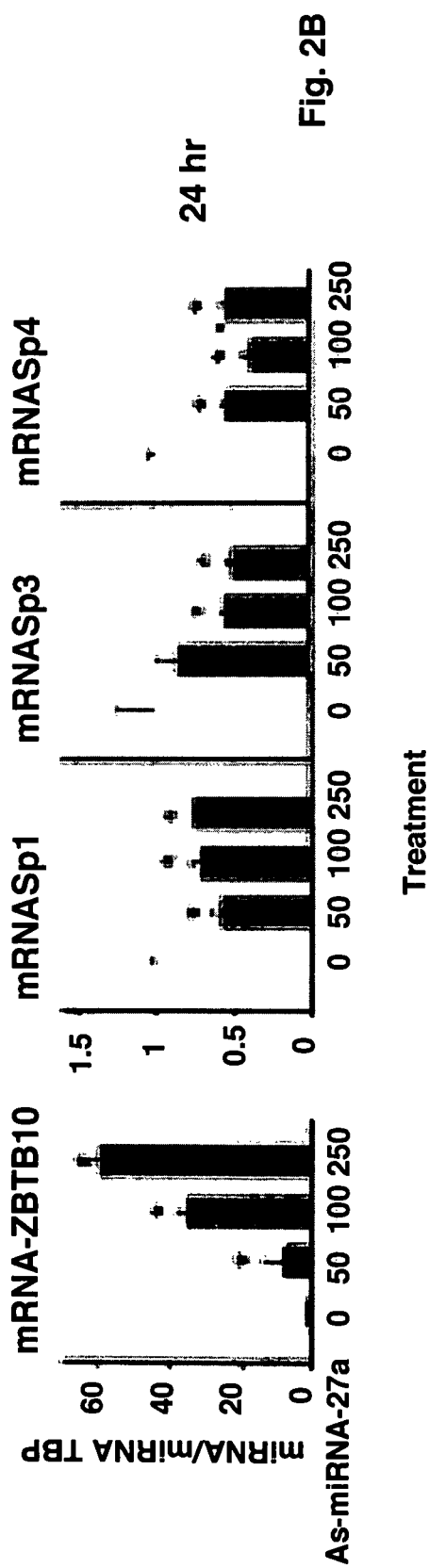
Fig. 2A
Fig. 2B

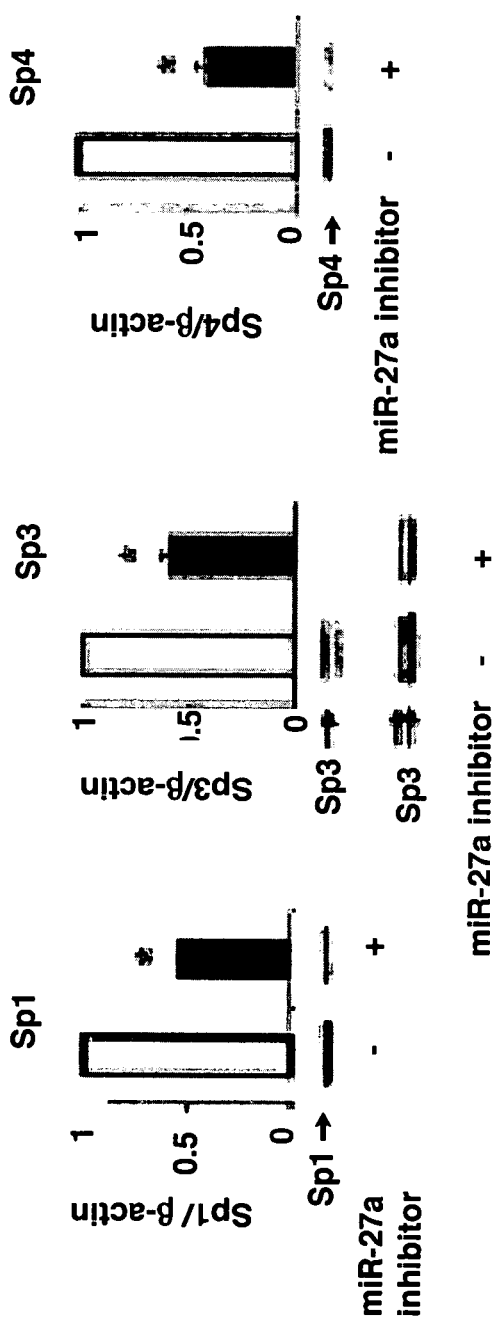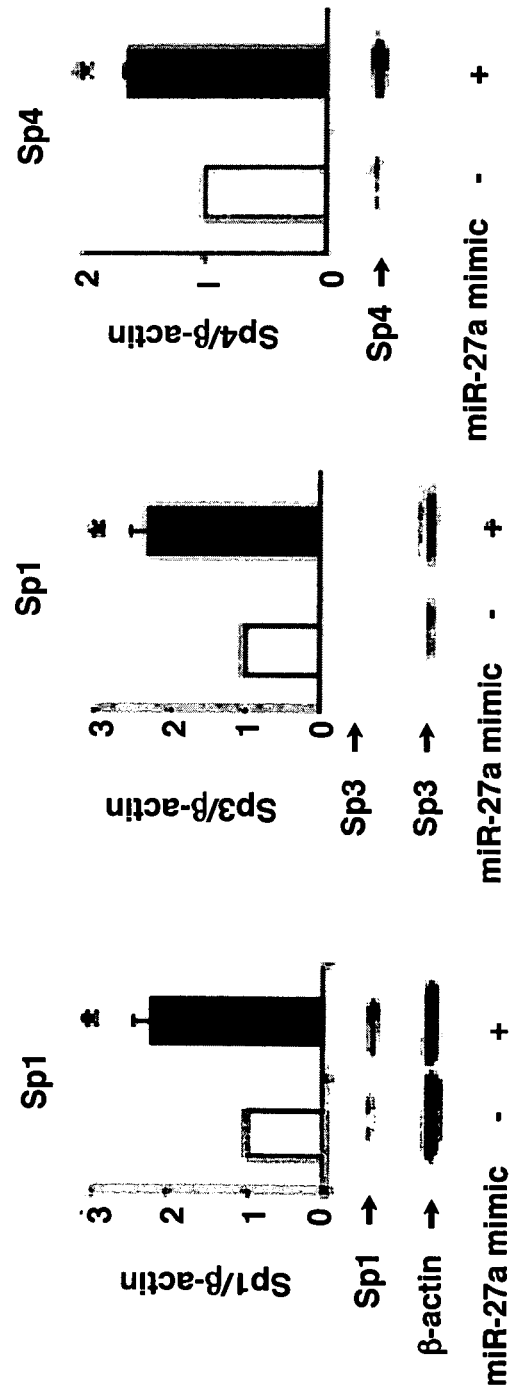

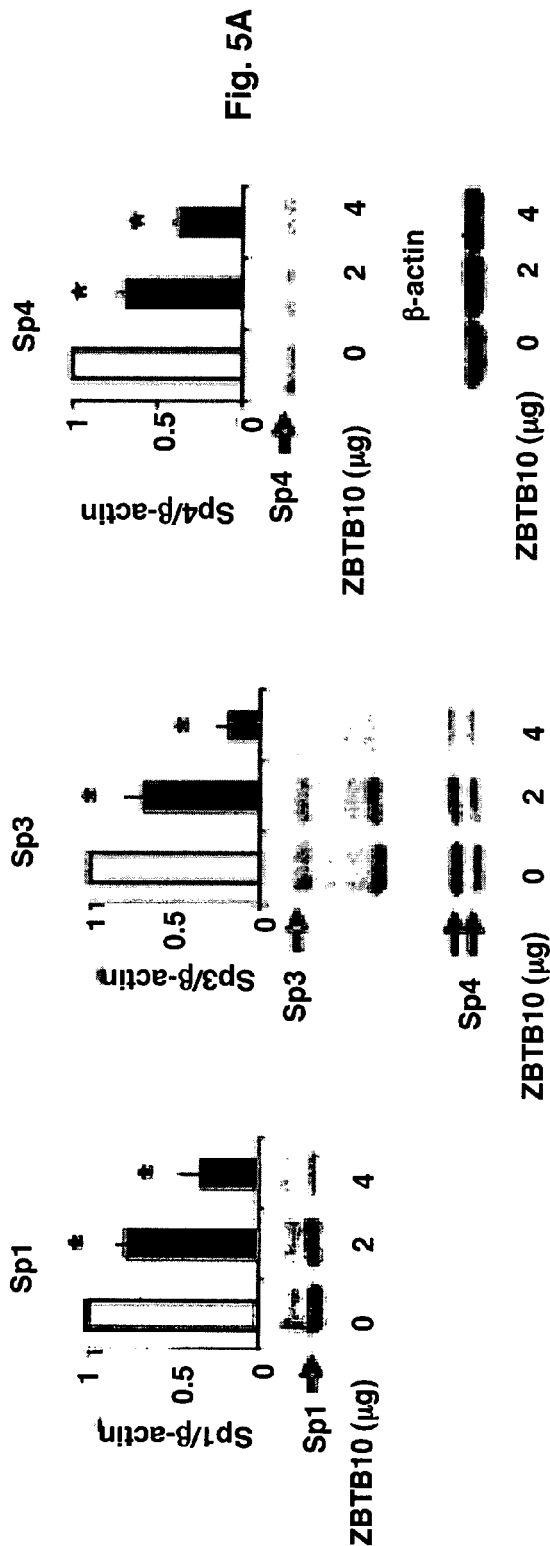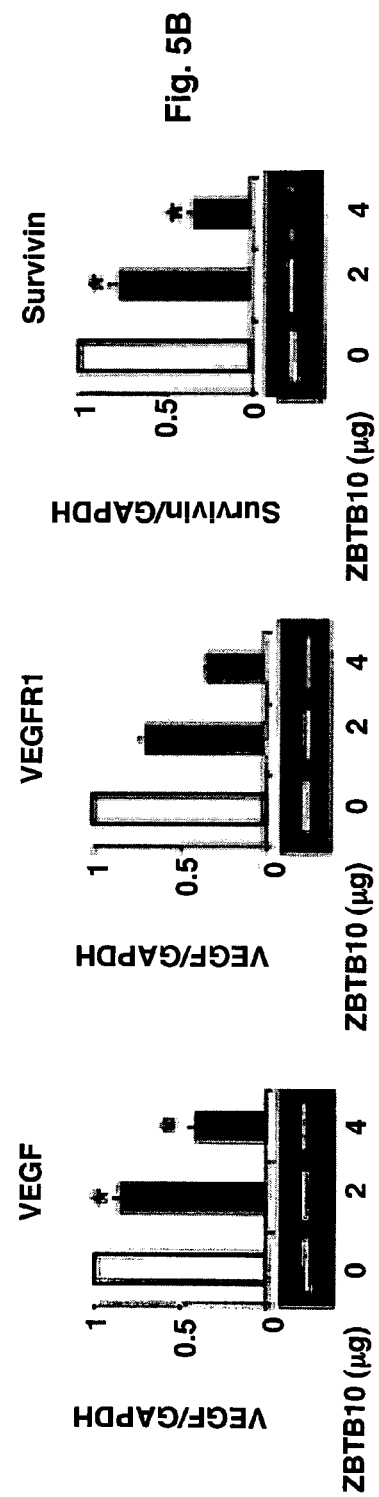
Fig. 5A
Fig. 5B

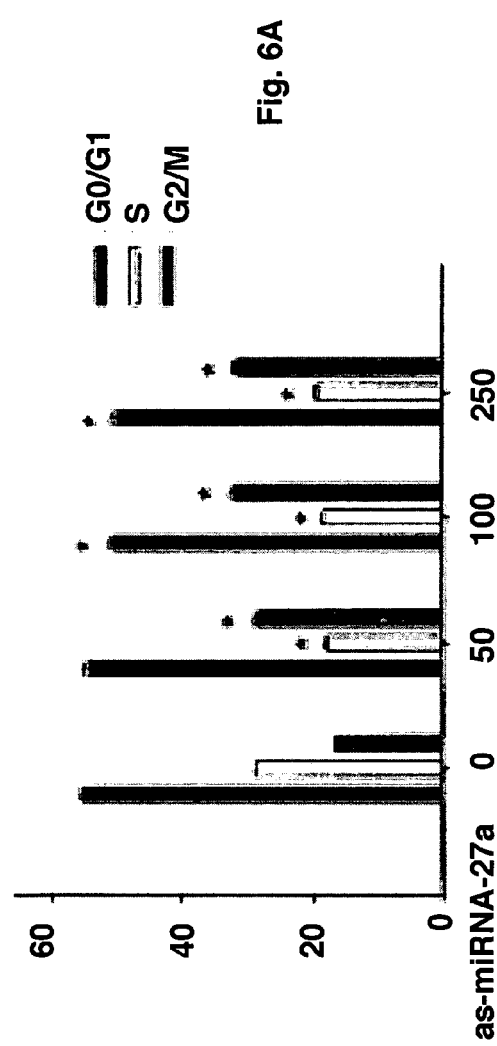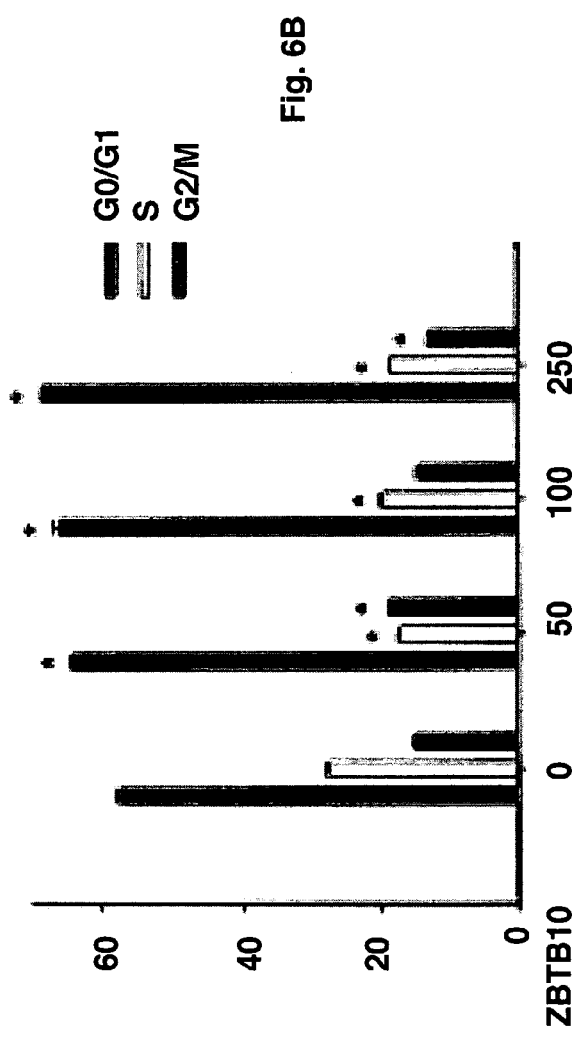

Fig. 7A
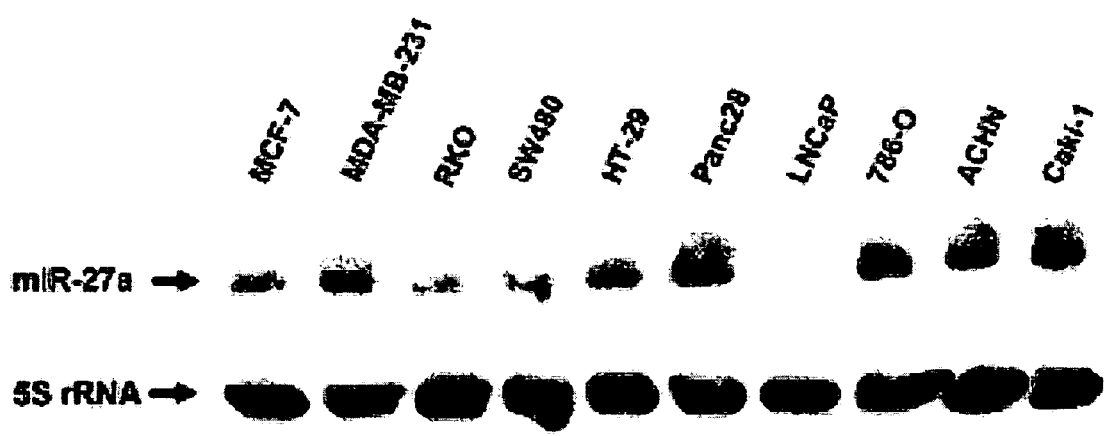
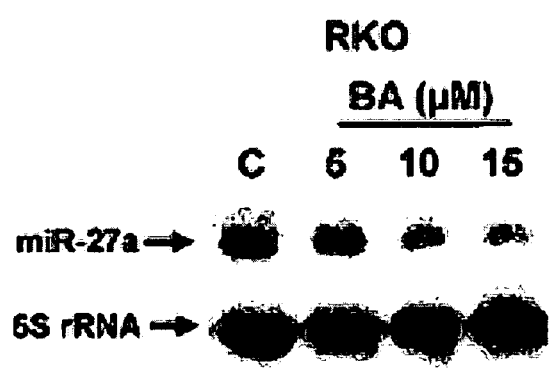
Fig. 7B

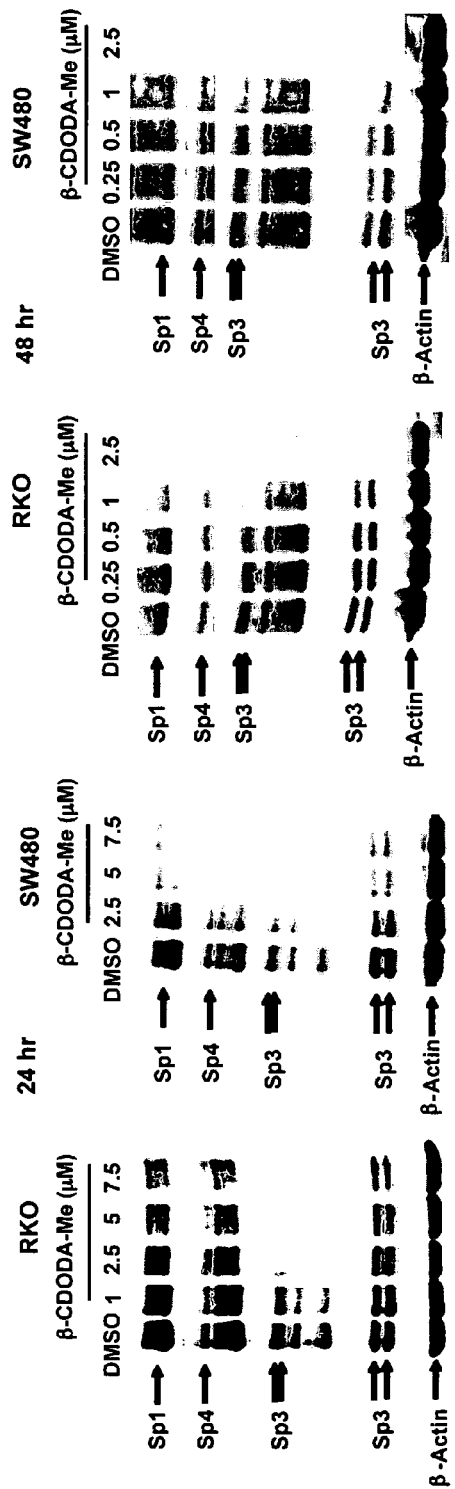
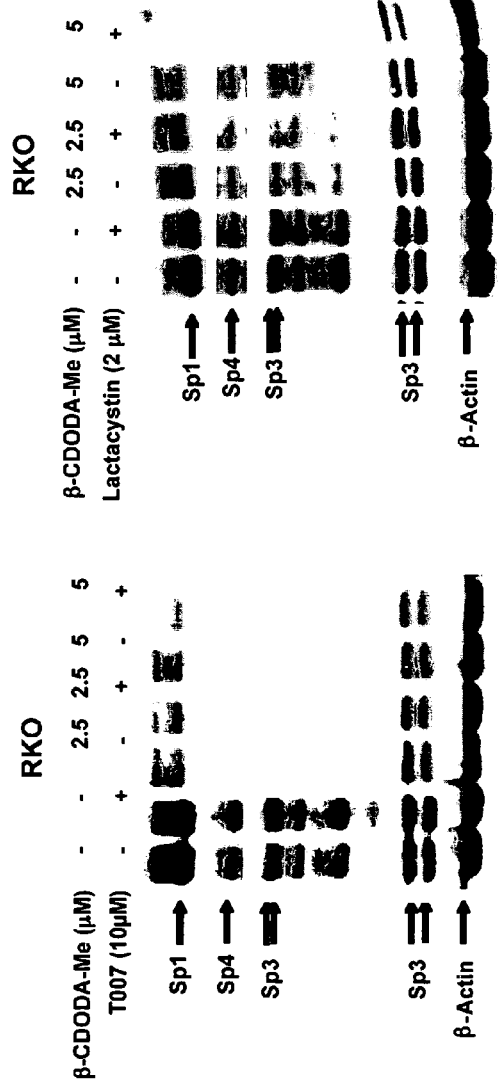
Fig. 8C
Fig. 8D

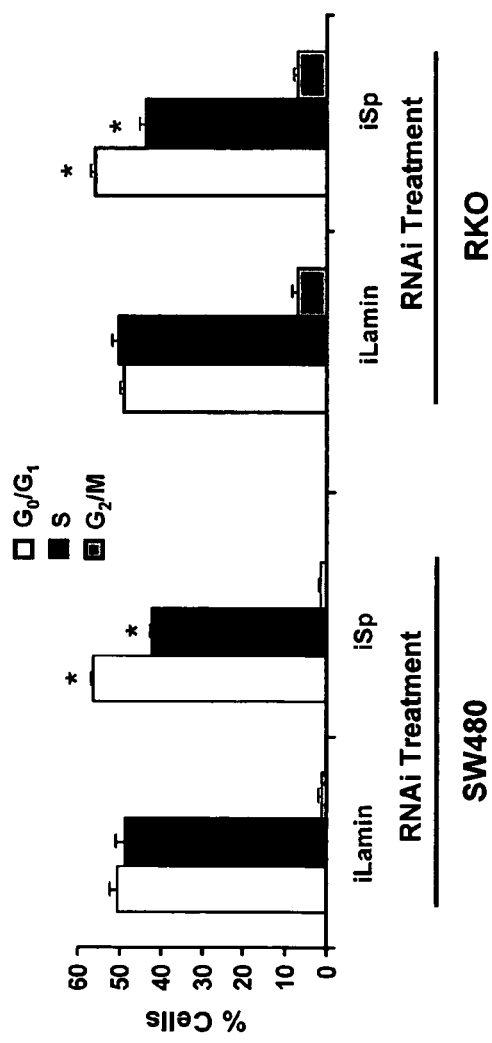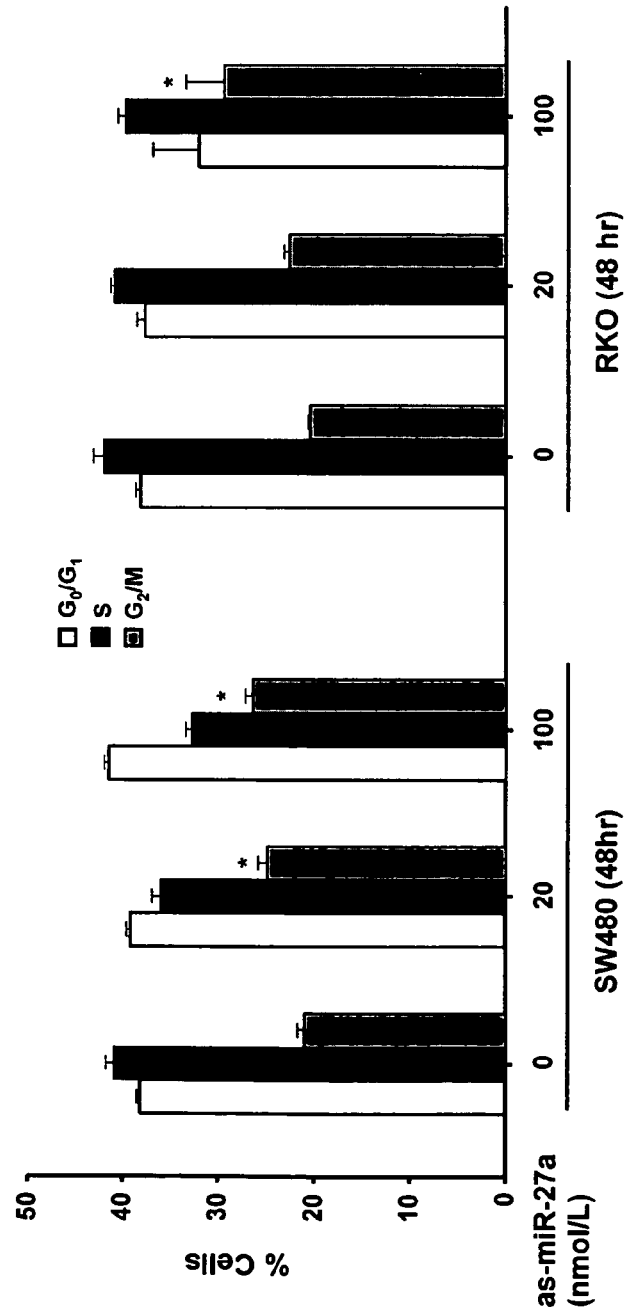

US 7,812,003 B2

ANTISENSE MICRORNA AND USES THEREFOR

CROSS REFERENCE TO RELATED APPLICATION

This non-provisional application claims benefit of provisional application U.S. Ser. No. 60/962,996 filed on Aug. 2, 2007.

FEDERAL FUNDING LEGEND

This invention was produced in part using funds obtained through National Institutes of Health grants ES09106, CA108718 and CA112337. Consequently, the federal government has certain rights in this invention.

BACKGROUND OF THE INVENTION

1. Field of the Invention

The present invention relates to the fields of molecular biology and oncology. Specifically, the present invention relates to, inter alia, methods for using antisense oligonucleotides to inhibit microRNA-27a suppression of the Sp repressor ZBTB10 in cancer cells.

2. Description of the Related Art

Specificity protein 1 (Sp1) was the first transcription factor identified (1,2) and is a member of the Sp/Kruppel-like factor (KLF) family of transcription factors (3-6). These proteins are characterized by their C-terminal domains which contain three C2H2-type zinc fingers that recognize GC/GT boxes in promoters of target genes. The N-terminal domains of Sp/KLF proteins are highly variable in both structure and function and many KLF proteins are truncated in this region. Some Sp/KLF members are critical for embryonic development and knockout of Sp1, Sp3 and Sp4 genes in mice results in embryo lethality or multiple developmental deficits (7-10). Sp and KLF proteins cooperatively interact with one another and other transcription factors on GC-rich promoters to activate or inhibit diverse classes of mammalian and viral genes that play a critical role in regulating cellular homeostasis (11).

The tissue- and age-dependent expression of Sp proteins in humans and laboratory animal models has not been extensively investigated, however, several studies report that Sp1 protein is overexpressed in tumor vs. non-tumor tissues (12-19). For example, in gastric cancer Sp1 expression was observed in tumor cells; whereas in stromal and normal glandular cells, Sp1 expression was either weak or non-detectable (12). Moreover, survival of gastric cancer patients increased with decreasing Sp1 protein expression. Malignant transformation of human fibroblasts resulted in an 8- to 18-fold increase in Sp1 expression and the transformed cells formed tumors in athymic nude mouse xenografts, whereas Sp1 knockdown gave cells that were non-tumorigenic in the same mouse xenograft model (19).

Although Sp1 is widely expressed in tumors, there is increasing evidence that Sp3 and Sp4 also are expressed in cancer cells and contribute to Sp dependent procarcinogenic responses (20-25). Using RNA interference, it was shown that Sp1 knockdown using a small inhibitory RNA (siRNA) for Sp1 (iSp1) inhibited G0/G1 to S phase progression in MCF-7 breast cancer cells (25). SiRNAs for Sp3 (iSp3) and Sp4 (iSp4) were used along with iSp1 to show that in pancreatic cancer cells, Sp1, Sp3 and Sp4 proteins regulated expression of vascular endothelial growth factor (VEGF), VEGF receptor 1 (VEGFR1 or Flt) and VEGFR2 (KDR) (20-22). Moreover, Sp3 acted as a repressor of p27 in pancreatic cancer cells (21), indicating that overexpression of Sp proteins in cancers contribute to their proliferative and angiogenic phenotype. The underlying factors associated with high expression of Sp proteins, such as Sp1, Sp3 and Sp4 in tumors are not well understood.

The underlying factors associated with high expression of Sp proteins such as Sp1, Sp3 and Sp4 in tumors are not well understood. It is contemplated that microRNAs (miRNAs) may play a role in mediating overexpression of these transcription factors in tumors and cancer cells. mRNAs are small noncoding RNAs that regulate expression of genes by specifically interacting with 3'-untranslated regions of target gene mRNAs to repress translation or enhance mRNA cleavage (26, 27). It was observed that miRNA-27a (miR-27a) may have affected ZBTB10/RINZF expression; however, the extent of this interaction was not quantitated (28). This novel zinc finger protein (ZBTB10) inhibits activation of the GC-rich gastrin gene promoter (29).

There is a recognized need in the art for improved cancer therapies. Specifically, the prior art is deficient in methods utilizing antisense or related technologies to inhibit miR-27a suppression genes such as ZBTB10 which would repress overexpression of Sp proteins and other Sp-dependent genes/proteins in tumors or cancer cells. The present invention fulfills this long standing need in the art.

SUMMARY OF THE INVENTION

The present invention is directed to a method for suppressing specificity protein (Sp) activity in a cell associated with a cell proliferative disease. The method comprises increasing expression of one or both of an Sp repressor gene or one or more genes effective to induce cell cycle arrest in the cell. For example, one may contact a microRNA in the cell with a microRNA antisense oligonucleotide, thereby increasing expression of the gene(s) while decreasing expression of the microRNA.

The present invention also is directed to a method for inhibiting expression of a microRNA in a cancer cell. The method comprises delivering a microRNA antisense oligonucleotide to the cancer cell. The microRNA antisense oligonucleotide is delivered to the cancer cell via a cationic lipid, a polymer complex or a liposome.

The present invention is directed further to a method of treating a cancer in a subject. The method comprises administering a pharmacologically effective amount of an antisense microRNA-27A oligonucleotide to the subject thereby treating the cancer. The microRNA-27a antisense oligonucleotide may have the sequence shown in SEQ ID NO: 1 or SEQ ID NO: 2.

The present invention is directed further still to the antisense oligonucleotide having the sequence shown in SEQ ID NO: 1 or SEQ ID NO: 2.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 1A-1C illustrate expression of miR-27a, ZBTB10, and Sp proteins in breast cancer cell lines. FIG. 1A shows the relative expression of miR-27a and let-7a. Expression of miR-27a and let-7a microRNAs in ZR-75, MCF-7 BT474, MDA-MB-435, MDA-MB-231 and SKBR3 breast cancer cell lines was determined by real time PCR. Results are expressed as means±SE for three replicate determinations for each cell line. MiR-27a and let-7a levels were normalized to miR-49 and similar results were obtained using U6 snRNA for normalization. FIG. 1B shows expression of ZBTB10 and Sp mRNA levels in breast cancer cells. Expression of ZBTB10, Sp1, Sp3 and Sp4 mRNA levels in the panel of six breast cancer cell lines was determined by real time PCR. Results are expressed as means±SE for three replicate determinations for each cell line. FIG. 1C shows Sp protein expression. Whole cell lysates were obtained from the panel of breast cancer cell lines. Sp1, Sp3 and Sp4 protein expression was determined by Western blot analysis. Relative expression of proteins Sp1, Sp3 and Sp4 also was determined in normal MCF10A cells and compared to T47D cells.

FIGS. 2A-2D illustrate effects of as-miR-27a on ZBTB10, Sp1, Sp3 and Sp4 expression in MDA-MB-231 cells. FIG. 2A shows the specificity of as-miR-27a. MDA-MB-231 cells were transfected with 0-250 ng as-miR-27a and analyzed for miR-27a, let-7a and miR-17-5p expression by real time PCR. Results are expressed as means±SE for three replicate determinations for each microRNA and significantly (p<0.05) decreased activity is indicated by an asterisk. FIG. 2B shows that as-miR-27a decreases ZBTB10 and Sp expression. MDA-MB-231 cells were transfected with 100 ng as-miR-27a and after 24 hr, ZBTB10, Sp1, Sp3 and Sp4 mRNA levels were determined by real time PCR. Results are expressed as means±SE and significantly (p<0.05) decreased expression is indicated by an asterisk. As-miR-27a decreases Sp1 (FIG. 2C) and Sp3 (FIG. 2D) promoter activity. MDA-MB-231 cells were transfected with as-miR-27a and Sp1 promoter constructs and luciferase activity was determined. Results are expressed as means±SE for three replicate determinations for each treatment group and significantly (p<0.05) decreased activity is indicated by an asterisk.

FIGS. 3A-3D illustrate the role of miR-27a in expression of Sp and Sp-dependent genes/proteins. As-miR-27a decreases (FIG. 3A) and miR-27a mimic (FIG. 3B) increases of Sp1, Sp3 and Sp4 proteins. MDA-MB-231 cells were transfected with 100 ng/ml as-miR-27a or the mimic and after 24 hr, whole cell lysates were analyzed by Western blot analysis for Sp1, Sp3 and Sp4 proteins as described. Relative protein expression was normalized to beta-actin and levels in control cells were set at 1.0. Results are expressed as means±SE for at least three replicate determinations for each treatment group and significantly decreased (FIG. 3A) or increased (FIG. 3B) protein expression is indicated by an asterisk. FIG. 3C shows expression of Sp-dependent proteins/responses. MDA-MB-231 cells were transfected with 100 ng/ml as-miR-27a and protein expression was determined as in FIG. 3A. Results are expressed as means±SE for three replicate determinations for each treatment group and significantly (p<0.05) decreased expression is indicated by an asterisk. FIG. 3D shows the effects of as-miR-27a on survivin, VEGF and VEGFR1 mRNA expression. MDA-MB-231 cells were transfected with as-miR-27a and mRNA levels were determined by real time PCR. Results were expressed as means±SE for three replicate determinations for each treatment group and significantly (p<0.05) decreased activity is indicated by an asterisk.

FIG. 4A shows that ZBTB10 decreases Sp mRNA levels. MDA-MB-231 cells were transfected with different amounts of ZBTB10 expression plasmid and after 24 hr, mRNA was extracted and levels of expression were determined by semi-quantitative RT-PCR. Results were expressed as means±SE for three replicate determinations for each treatment group and significantly (p<0.05) decreased/increased mRNA levels (normalized to GADPH mRNA) compared to cells not transfected with ZBTB10 are indicated by an asterisk. ZBTB10 expression decreases Sp1 (FIG. 4B) and Sp3 (FIG. 4C) promoter activity. MDA-MB-231 cells were transfected with various constructs and ZBTB10 expression plasmid and luciferase activity is determined. Results are expressed as means±SE for three replicate determinations for each treatment group and significantly (p<0.05) decreased activity is indicated by an asterisk.

FIGS. 5A-5C illustrate that ZBTB10 decreases expression of Sp proteins and Sp-dependent angiogenic and survival genes. FIG. 5A shows that ZBTB10 expression decreases expression of Sp1, Sp3 and Sp4 proteins. MDA-MB-231 cells were transfected with ZBTB10 expression plasmid and after 24 hr whole cell lysates were analyzed by Western blots. Results are expressed as means±SE for three replicate determinations for each treatment group and significantly (p<0.05) decreased protein expression is indicated by an asterisk. ZBTB10 decreases expression of angiogenic/survival genes (FIG. 5B) and proteins (FIG. 5C). MDA-MB-231 cells were transfected with ZBTB10 expression plasmid and after 24 hr, mRNA and protein were extracted and analyzed by semi-quantitative RT-PCR and Western blots, respectively. Results are expressed as means±SE for three replicate determinations for each treatment group and significantly (p<0.05) decreased activity as indicated by an asterick.

FIGS. 6A-6D illustrate modulation of the cell cycle by as-miR-27a and ZBTB10. MDA-MB-231 cells were transfected with as-miR-27a (100 ng) (FIG. 6A) or ZBTB10 expression plasmid (FIG. 6B). After 24 hr, cells were examined by FACS analysis and the percentage of cells in G0/G1, S and G2/M phases of the cell cycle were determined. Results are expressed as means±SE for three replicate determinations for each treatment group and significant (p<0.05) changes induced by as-miR-27a or ZBTB10 compared to control cells as indicated by an asterisk. The effects of as-miR-27a on cdc2 inhibitors Myt-1 and Wee-1 mRNA and cdc2 protein phosphorylation are shown in FIG. 6C. MDA-MB-231 cells were treated for 24 hr with as-miR-27a (100 ng/ml) and mRNA levels (real time PCR) and cdc2/phospho-cdc2 protein (Western blot) were determined. Results for mRNA levels are expressed as means±SE for three replicate determinations for each treatment group and significant (p<0.05) induction as indicated by an asterisk. Phosphorylated cdc2 (FIG. 6D) was increased by approximately 2-fold in replicate experiments.

FIGS. 7A-7B illustrate miR-27a expression and effects of betulinic acid on miR-27a. Northern blot analysis shows that miR-27a is expressed in breast (MCF-7, MDA-MB-231), colon (RKO, SW480 and HT-29), pancreatic (Panc28) and kidney (786-0, ACHN and Caki-1) cancer cells, but not in LNCaP cells (FIG. 7A). Treatment of RKO cells with betulinic acid decreased miR-27a levels (FIG. 7B) and similar results have been observed in other cancer cell lines using CDODA-Me and tolfenamic acid.

FIGS. 8A-8D (F1 of paper) show that β-CDODA-Me inhibits growth, induces apoptosis, and degradation of Sp proteins. FIG. 8A: Decreased cell survival in RKO cells. Cells were seeded and treated with solvent (DMSO) or different concentrations of β-CDODA-Me (0.5-5 μM) alone or in combination with T007 for 4 days. Cell survival is expressed as the percentage of β-CDODA-Me-treated cells remaining compared to DMSO (set at 100%). Results are expressed as means±SE for three replicate determinations for each treatment group and significantly (p<0.05) decreased survival is indicated by an asterisk. Similar results were observed for SW480 cells. Induction of apoptosis (FIG. 8B) and decreased expression of Sp1, Sp3 and Sp4 (FIG. 8C, 8D). RKO and SW480 cells were treated with DMSO, 13-CDODA-Me (1-5 μM), T007 (10 μM), Lactacystin (2 μM), or combinations as indicated for 24 hr or 48 hr and whole cell lysates were analyzed by Western blot analysis.

FIGS. 10A-10D shows the effects of β-CDODA-Me and as-miR27a. β-CDODA-Me decreases miR-27a (FIGS. 10A-10B) and increases ZBTB10 (FIG. 10C) expression. RKO and SW480 colon cancer cells were treated with DMSO or different concentrations of β-CDODA-Me and after 18 hr, total RNA was extracted and analyzed for miR27a by real time PCR and ZBTB10 by semi-quantitative RT-PCR. Northern blot analysis also showed that CDODA-Me decreased miR-27a. FIG. 10D: as-miR27a decreases Sp1, Sp4 and Sp3 proteins. RKO cells were transfected with 50 and 100 ng as-miR27a and after 24 hr, whole cell lysates were analyzed by Western blot analysis for Sp1, Sp4 and Sp3 proteins.

FIG. 12C: iSp modulates Sp protein expression and the cell cycle in SW480 and RKO cells. Cells were transfected with iSp, a combination of small inhibitory RNAs for Sp1, Sp3 and Sp4 or a non-specific oligonucleotide (iLamin), and analyzed for Sp proteins by Western blots (to confirm Sp knockdown) and FACS analysis. FIG. 12D: as-miR-27a modulates the cell cycle. SW480 and RKO cells were transfected with different amounts of as-miR-27a and, after 48 hr, analyzed by FACS. All experiments in FIGS. 12A-12D were repeated three times, and results are expressed as means±SE. Significant (p<0.05) changes compared to untreated (0) or iLamin-treated cells are indicated by asterisks.

DETAILED DESCRIPTION OF THE INVENTION

Figure 1C:
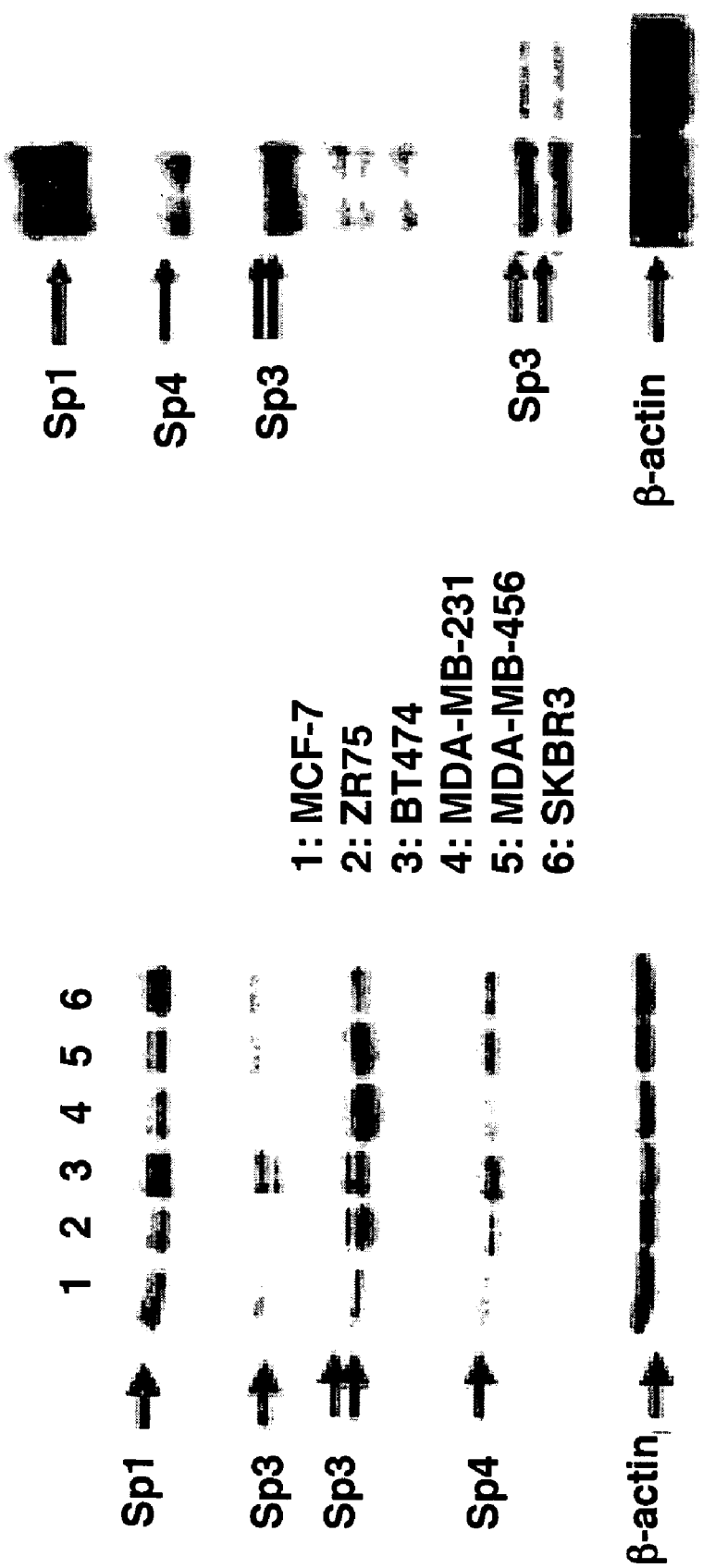

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any device or method described herein can be implemented with respect to any other device or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "treating" or the phrase "treating a cancer" includes, but is not limited to, halting the growth of cancer cells, killing the cancer cells or a mass comprising the same, or reducing the number of cancer cells or the size of a mass comprising the same. Halting the growth refers to halting any increase in the size or the number of cancer cells or in a mass comprising the same or to halting the division of the cancer cells. Reducing the size refers to reducing the size of a mass comprising the cancer cells or the number of or size of the same cells. As would be apparent to one of ordinary skill in the art, the term "cancer" or "cancer cells" or "tumor" refers to examples of neoplastic cell proliferative diseases and refers to a mass of malignant neoplastic cells or a malignant tissue comprising the same.

As used herein, the term "subject" refers to any recipient of a treatment using an antisense microRNA or a treatment given for a similar purpose as described herein.

In one embodiment of the present invention, there is provided a method for suppressing specificity protein (Sp) activity in a cell associated with a cell proliferative disease, comprising increasing expression of one or both of an Sp repressor gene or one or more genes effective to induce cell cycle arrest in the cell.

In this embodiment, the increasing step may comprise contacting a microRNA in the cell with a microRNA antisense oligonucleotide thereby increasing expression of the gene(s). Also a representative microRNA may be microRNA-27a. In addition the antisense microRNA-27a may have a representative sequence such as is shown in SEQ ID NO: 1 or SEQ ID NO: 2. Furthermore, one or more of the antisense nucleotides may be modified with a stabilizing group. Representative examples of stabilizing groups are one or more of a morpholino group, a 2'-O-methyl group or a phosphorothioate derivative. Alternatively, one or more nucleotides per se may be modified.

Also, in this embodiment the Sp repressor gene may be ZBTB10. The Sp protein may be Sp1, Sp3 or Sp4 or other Sp/KLF genes/proteins. In addition the gene effective to induce cell cycle arrest may be Myt-1. Myt-1 induces G2/M cell cycle arrest. Furthermore, the cell proliferative disease may be a cancer. Representative examples of a cancer are a bladder cancer, a kidney cancer, a prostate cancer, a gastrointestinal cancer, a pancreatic cancer, a melanoma, or a breast cancer.

In another embodiment of the present invention there is provided a method for inhibiting expression of a microRNA in a cancer cell, comprising delivering a microRNA antisense oligonucleotide to the cancer cell. In this embodiment the delivery step may comprise associating the antisense microRNA with a cationic lipid, a polymer complex or a liposome effective to target the cell. Also, the antisense microRNAs and the sequences and the modifying groups thereof and the cancer cells are as described supra.

In yet another embodiment of the present invention there is provided a method of treating a cancer in a subject, comprising administering a pharmacologically effective amount of an antisense microRNA-27a oligonucleotide to the subject thereby treating the cancer. The antisense microRNA-27a sequences and modifiers thereof and the cancers are as described supra.

In yet another embodiment of the present invention, there is provided an antisense microRNA-27a oligonucleotide having the sequence of SEQ ID NO: 1 or SEQ ID NO: 2. In this embodiment the nucleotides may be modified with one or more stabilizing groups. Alternatively, one or more nucleotides per se may be modified. Representative examples of the stabilizing group are a morpholino group, a 2'-O-methyl group or a phosphorothioate derivative.

Provided herein are methods of inhibiting the expression of microRNAs in cells associated with cell proliferative or neoplastic diseases. Targeted antisense degradation of microRNAs, e.g., microRNA-27a, decreases Sp and Sp-dependent gene expression and inhibiting cells at G2/M (a G2/M block) thereby inhibiting growth of these cells such as those comprising cancers or tumors. Effectively, microRNA degradation results in induction of cell death or apoptosis, growth inhibition and antiangiogenesis, decreased tumor growth and metastasis.

Without being limiting, representative examples of antisense microRNA-27a oligonucleotide sequences may be 5'-CCA CAC CAA GUC GUG UUC ATT-3' (SEQ ID NO: 1) and 5'-UGA ACA CGA CUU GGU GUG GTT-3' (SEQ ID NO: 2). As is known in the art an antisense RNA oligonucleotide complements all or part of the microRNA sequence and is of sufficient length that hybridization to the microRNA prevents its interaction with Sp repressor and other regulator genes such at Myt-1 and Wee-1. Also, the antisense oligonucleotides may be stabilized using various derivatives including one or more of a morpholino group, a 2-O-methyl group and phosphorothiorate derivatives. In addition one or more of the nucleotides comprising the oligonucleotide may be modified per se. Delivery of the antisense oligonucleotides may be achieved via cationic lipids, polymer complexes, liposomes, and other representative procedures well known and standard in the art (44-46) which are effective to target and/or contact a cell of interest.

Thus, the antisense RNA oligonucleotides provided herein are useful as therapeutics or chemotherapeutics to inhibit growth of abnormally proliferating cells in a neoplastic or cell proliferative disease by increasing expression of an Sp suppressor, e.g., ZBTB10, thereby inducing degradation of Sp proteins, e.g., Sp1, Sp3 and Sp4 and Sp-dependent genes in the cell. It is contemplated that contacting the abnormally proliferating or neoplastic cells with one or more of these compounds is effective to induce at least apoptosis in the cells and/or cell cycle arrest. Thus, the antisense oligonucleotides of the present invention are useful in treating cancers in a subject. It also is contemplated that the therapeutic effect would result in inhibition of metastasis of the cancer cells and/or inhibit angiogenesis. Preferably the subject is a mammal, more preferably the subject is a human. Representative examples of cancers are, although not limited to, genitourinary cancers, such as a bladder cancer, a kidney cancer or prostate cancer, gastrointestinal cancers, pancreatic cancers, melanomas, or breast cancers.

Dosage formulations of the antisense oligonucleotides associated with a delivery vehicle, such as cationic lipids, polymer complexes or liposomes, may comprise conventional non-toxic, physiologically or pharmaceutically acceptable carriers or other vehicles suitable for the method of administration. These antisense oligonucleotides or pharmaceutical compositions thereof may be administered independently one or more times to achieve, maintain or improve upon a pharmacologic or therapeutic effect derived from these antisense oligonucleotides. It is well within the skill of an artisan to determine dosage or whether a suitable dosage comprises a single administered dose or multiple administered doses. An appropriate dosage depends on the subject's health, the progression or remission of the cancer or cell proliferative disease, the route of administration and the formulation used.

The following example(s) are given for the purpose of illustrating various embodiments of the invention and are not meant to limit the present invention in any fashion.

EXAMPLE 1

Plasmids, Antibodies and Reagents

Sp1 and Sp3 promoter constructs were provided by Drs. Carlos Cuidad and Veronique Noe (University of Barcelona, Barcelona, Spain). The pVEGF-133 construct contain VEGF promoter insert (positions −131 to +54) linked to luciferase reporter gene. The pSurvivin-269 was provided by Dr. M. Zhou (Emory University, Atlanta, Ga.). The pCMV6-XL4-ZBTB10 expression vector and empty vector (pCMV6-XL4) were from Origene (Rockville, Md.). Antibodies for Sp1, Sp3, Sp4, VEGF and VEGFR1 were purchased from Santa Cruz Biotechnology, Inc. (Santa Cruz, Calif.). c-PARP and survivin antibodies were from Cell Signaling Technology Inc. (Danvers, Mass.). Monoclonal β-actin antibody was purchased from Sigma-Aldrich. Reporter lysis buffer, and luciferase reagent for luciferase studies were supplied by Promega (Madison, Wis.). β-Galactosidase (i-Gal) reagent was obtained from Tropix (Bedford, Mass.), and LipofectAMINE 2000 reagent was purchased from Invitrogen (Carlsbad, Calif.). Western Lightning chemiluminescence reagent was obtained from PerkinElmer Life and Analytical Sciences (Boston, Mass.). The PPARγ N-(4'-aminopyridyl)-2-chloro-5-nitrobenzamide (T007) were synthesized in this laboratory, and their identities and purity (>98%) were confirmed by gas chromatography-mass spectrometry.

Cell Proliferation and Transfection Assay and Western Blot Analysis

RKO and SW480 colon cancer cells ($2\times10^4$ per well) were plated in 12-well plates and allowed to attach for 24 hr. The medium was then changed to DMEM/Ham's F-12 medium containing 2.5% charcoal-stripped FBS, and either vehicle (DMSO) or different concentrations of the compound were added. Fresh medium and compounds were added every 48 hr, and cells were then trypsinized and counted after 48 and 96 hr using a Coulter Z1 cell counter. Transfection experiments in RKO and SW480 cells used 0.4 µg of reporter gene constructs and 0.04 µg of β-Gal and LipofectAMINE 2000 reagent (Invitrogen). Results of cell proliferation and transfection studies are expressed as means±S.E. for at least three replicate determinations for each treatment group. Western blots were determined with whole cell lysates essentially.

Northern Blot Analysis

For miRNA analysis, 20 µg total RNA per lane was electrophoresed on 15% TBE urea polyacryalminde gel (Invitrogen), electrophoretically transferred in 0.5×TBE at 300 mA for 45 minutes to GeneScreen Plus membrane (PerkinElmer, Boston, Mass.), UV cross-linked, and hybridized in ULTRAhyb-Oligo hybridization buffer (Ambion, Austin, Tex.) at 42° C. with $^{32}$P end-labeled DNA oligonucleotides complementary to the miRNA under examination. Blots were washed at 42° C. in 2×SSC and 0.5% SDS for 30 min with gentle agitation.

Semiquantitative RT-PCR

RKO and SW480 colon cancer cells were transfected with either as-miRNA-27a or with pCMV6-XL4 control and pCMV6-XL4-ZBTB10 expression plasmid using Lipofectamine 2000 following manufacturer's protocol. Total RNA was extracted using RNeasy Mini Kit (Qiagen, Inc.), and 2 µgm of RNA was used to synthesize cDNA using Reverse Transcription System (Promega). Primers were obtained from IDT and used for amplification were as follows: Sp1 (sense 5'-ATG GGG GCA ATG GTA ATG GTG G-3' (SEQ ID NO: 3); antisense 5'-TCA GM CTT GCT GGT TCT GTA AG-3' (SEQ ID NO: 4), Sp3 (sense 5'-ATG ACT GCA GGC ATT AAT GCC G-3' (SEQ ID NO: 5); antisense 5'-TGT CTC TTC AGA AAC AGG CGA C-3') (SEQ ID NO: 6), Sp4 (sense 5'-ATG GCT ACA GM GGA GGG AM AC-3' (SEQ ID NO: 7); antisense 5'-TTG ACC AGG GGT GGA AGA ATT AC-3') (SEQ ID NO: 8), ZBTB10 (sense 5'-GCT GGA TAG TAG TTA TGT TGC-3' (SEQ ID NO: 9); antisense 5'-CTG AGT GGT TTG ATG GAC AGA G-3') (SEQ ID NO: 10), VEGF (sense 5'-CCA TGA ACT TTC TGC TGT CTT-3' (SEQ ID NO: 11); antisense 5'-ATC GCA TCA GGG GCA CAC AG-3') (SEQ ID NO: 12), VEGFR1 (sense 5'-ATG GAG CGT AAG AAA GM AAA ATG-3' (SEQ ID NO: 13); antisense 5'-TCA AGT ACC TCC TTT TCT CAC AT-3') (SEQ ID NO: 14), Survivin (sense 5'-ATG GCC GAG GCT GGC TTC ATC-3' (SEQ ID NO: 15); antisense 5'-ACG GCG CAC TTT CTT CGC AGT T-3') (SEQ ID NO: 16) and GAPDH (sense 5'-ACG GAT TTG GTC GTA TTG GGC G-3' (SEQ ID NO: 17); antisense 5'-CTC CTG GM GAT GGT GAT GG-3') (SEQ ID NO: 18). PCR products were electrophoresed on 1% agarose gels containing ethidium bromide and visualized under UV transillumination.

Quantitative Real-Time PCR of mRNA and miRNA cDNA was prepared from the RKO and SW480, cell lines using Reverse Transcription System (Promega). Each PCR was carried out in triplicate in a 20-µl volume using SYBR Green Mastermix (Applied Biosystems, Foster City, Calif.) for 15 min at 95° C. for initial denaturing, followed by 40 cycles of 95° C. for 30 s and 60° C. for 1 min in the Applied Biosystems 7900HT Fast Real-time PCR System. The ABI Dissociation Curves software was used following a brief thermal protocol (95° C. for 15 s and 60° C. for 15 s, followed by a slow ramp to 95° C.) to control for multiple species in each PCR amplification. Values for each gene were normalized to expression levels of TATA-binding protein. The primers used for real-time PCR were Myt-1 (sense 5'-CCT TCC AAG AGT AGC TCC AAT TC-3' (SEQ ID NO: 19); antisense 5'-GCC GGT AGC TCC CAT ATG G-3') (SEQ ID NO: 20) and TATA-binding protein (sense 5'-TGC ACA GGA GCC AAG AGT GM-3' (SEQ ID NO: 21); antisense 5'-CAC ATC ACA GCT CCC CAC CA-3') (SEQ ID NO: 22). miRNA was extracted using the mirVana miRNA extraction kit (Applied Biosystems). Quantification of miRNA (RNU6B and miRNA-27a) was done using the Taqman miRNA kit (Applied Biosystems) according to the manufacturer's protocol with real-time PCR. U6 small nuclear RNA was used as a control to determine relative miRNA expression.

Fluorescence-Activated Cell Sorting Analysis

RKO and SW480 cells were treated with either the vehicle (DMSO) or the compound for 24 hr or with as-miR27a. Cells were trypsinized, centrifuged, and resuspended in staining solution containing 50 µg/mL propidium iodide, 4 mmol/L sodium citrate and 30 units/mL RNase. After incubation at room temperature for 1 hr, cells were analysed on a FACS Vantage SE DiVa made by Becton Dickinson (BD), using BD FACSDiva Software V4.1.1. Propidium iodide (PI) fluorescence was collected through a 610SP bandpass filter, and list mode data were acquired on a minimum of 50,000 single cells defined by a dot plot of PI width vs. PI area. Data analysis was performed in BD FACSDiva Software V4.1.1 using PI width vs. PI area to exclude cell aggregates.

EXAMPLE 2

Expression of miR-27a and SP Proteins in Breast Cancer Cells

MiR-27a expression has been identified in multiple cancer cell lines by Northern blot analysis. FIG. 1A summarizes expression of miR-27a relative to miR-49 in ER-positive ZR-75, BT474 and MCF-7 and ER-negative MDA-MB-435, MDA-MB-231 and SKBR3 breast cancer cell lines. MiR-49, which was expressed in all cell lines, was used to normalize relative expression of miR-27a. Similar results were obtained using U6 snRNA as a normalizing RNA. The miR let-7 family are cancer-associated tumor suppressors (30-34). FIG. 1A also compares miR-27a and let-71 expression in breast cancer cells. Levels of the former miR tended to be higher in all six breast cancer lines. Using a similar approach, it was determined that expression of Sp1, Sp3, Sp4, and ZBTB10 mRNA, relative to TBP mRNA, and the Sp mRNAs were more highly expressed than ZBTB10 mRNA in the six cell lines (FIG. 1B). It has been demonstrated that Sp1, Sp3 and Sp4 proteins are expressed in breast cancer cells. FIG. 1C demonstrates expression of these three proteins in all six ER-positive and ER-negative breast cancer cell lines. Relative levels of Sp protein expression varied between cell lines. This was particularly evident for Sp4 which was lowest in MCF-7 and MDA-MB-231 cells among the ER-positive and -negative breast cancer cell lines, respectively. A comparison of Sp proteins expression in T47D cancer cells and in normal MCF10A breast cancer cells showed that Sp1, Sp3 and Sp4 are more highly expressed in cancer vs. non-cancer cell lines.

EXAMPLE 3

Effects of as-miR-27a on ZBTB10 and Sp mRNA and Promoter Expression

Figure 2C:
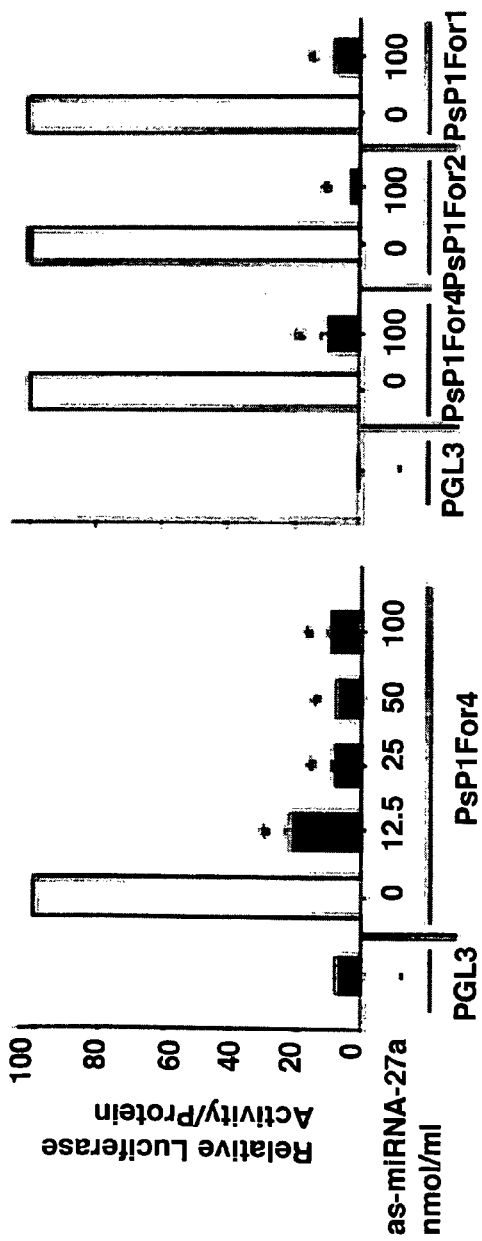
Figure 2D:
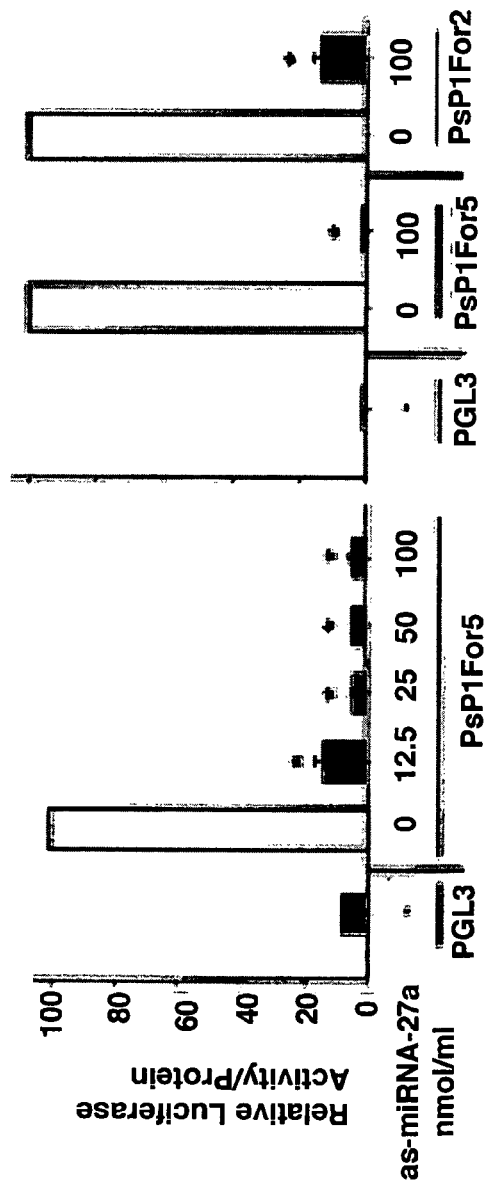

The role of miR-27a in mediating expression of ZBTB10 and the downstream effects of this Sp repressor were investigated using a miR-27a antisense construct in MDA-MB-231 cells. FIG. 2A demonstrates that antisense miR-27a (as-miR-27a) decreased miR-27a expression of miR-7a and miR-17-5p were unchanged, demonstrating the specificity of the antisense construct. Transfection with as-miR-27a in MDA-MB-231 cells also increased ZBTB10 mRNA levels (FIG. 2B). FIG. 2C summarizes the effects of as-miR-27a on transactivation in MDA-MB-231 cells transfected with pSp1For4 which contains the −751 to −20 region of the Sp1 gene promoter (35). This shows the dose-dependent decrease in luciferase activity in MDA-MB-231 cells transfected with pSp1For4 and 12.5-100 ng as-miR-27a. As-miR-27a decreased luciferase activity in MDA-MB-231 cells transfected with Sp1For4 and the Sp1For2 and Sp1For1 deletion constructs. Transfection of different amounts of as-miR-27a also decreased luciferase activity in MDA-MB-231 cells transfected with pSp3For5 which contains the −417 to −38 region of the Sp3 gene promoter (36). As-miR-27a also inhibited transactivation in cells transfected with pSpFor5 and the deletion construct pSp3For2 (FIG. 2D).

EXAMPLE 4

Effects of as-miR-27a on Sp Proteins, Sp-Dependent Genes/Proteins and Apoptosis

Figure 3C:
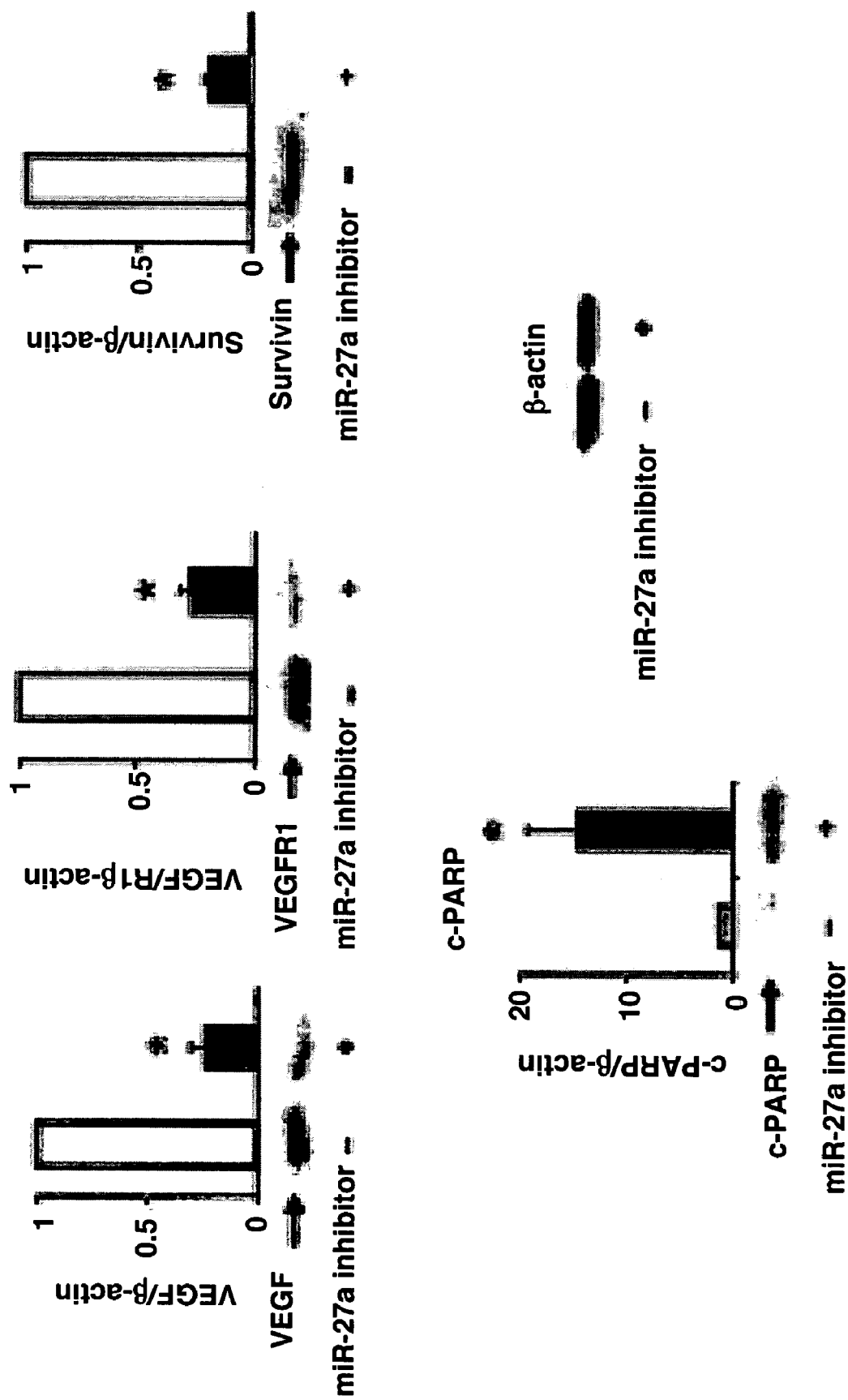
Figure 3D:
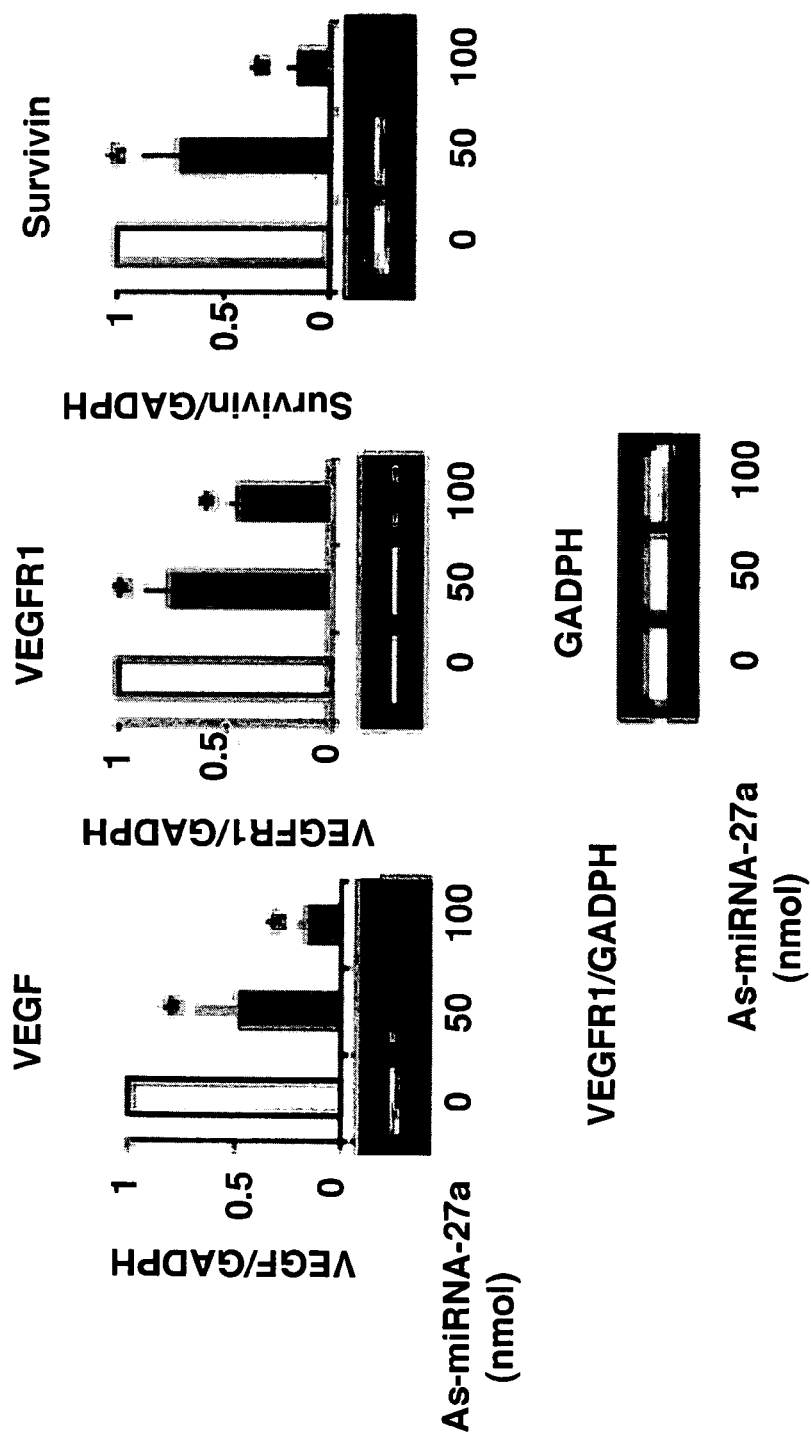

FIG. 3A shows that in MDA-MB-231 cells transfected with the as-miR-27a, there was decreased expression of Sp1, Sp3 and Sp4 proteins. In contrast, transfection with a miR-27a mimic enhanced expression of Sp1, Sp3 and Sp4 proteins (FIG. 3B) and demonstrated a direct correlation between miR-27a and Sp protein expression. It has been shown previously that Sp proteins regulate expression of survival and angiogenic genes (20-25,33). FIG. 3C shows that after transfection of cells with as-miR-27a, there was an increase in PARP cleavage and a decrease in expression of the antiapoptotic protein survivin and the antiangiogenic proteins VEGF and VEGFR1 and a parallel decrease in survivin, VEGF and VEGFR1 mRNA (FIG. 3D). These results are consistent with decreased expression of Sp proteins (FIG. 3A) since VEGF, VEGFR1 and survivin are Sp-dependent genes (20-25,37).

EXAMPLE 5

Effects of ZBTB10 on Sp mRNA Expression and Promoter Activity

Figure 4A:
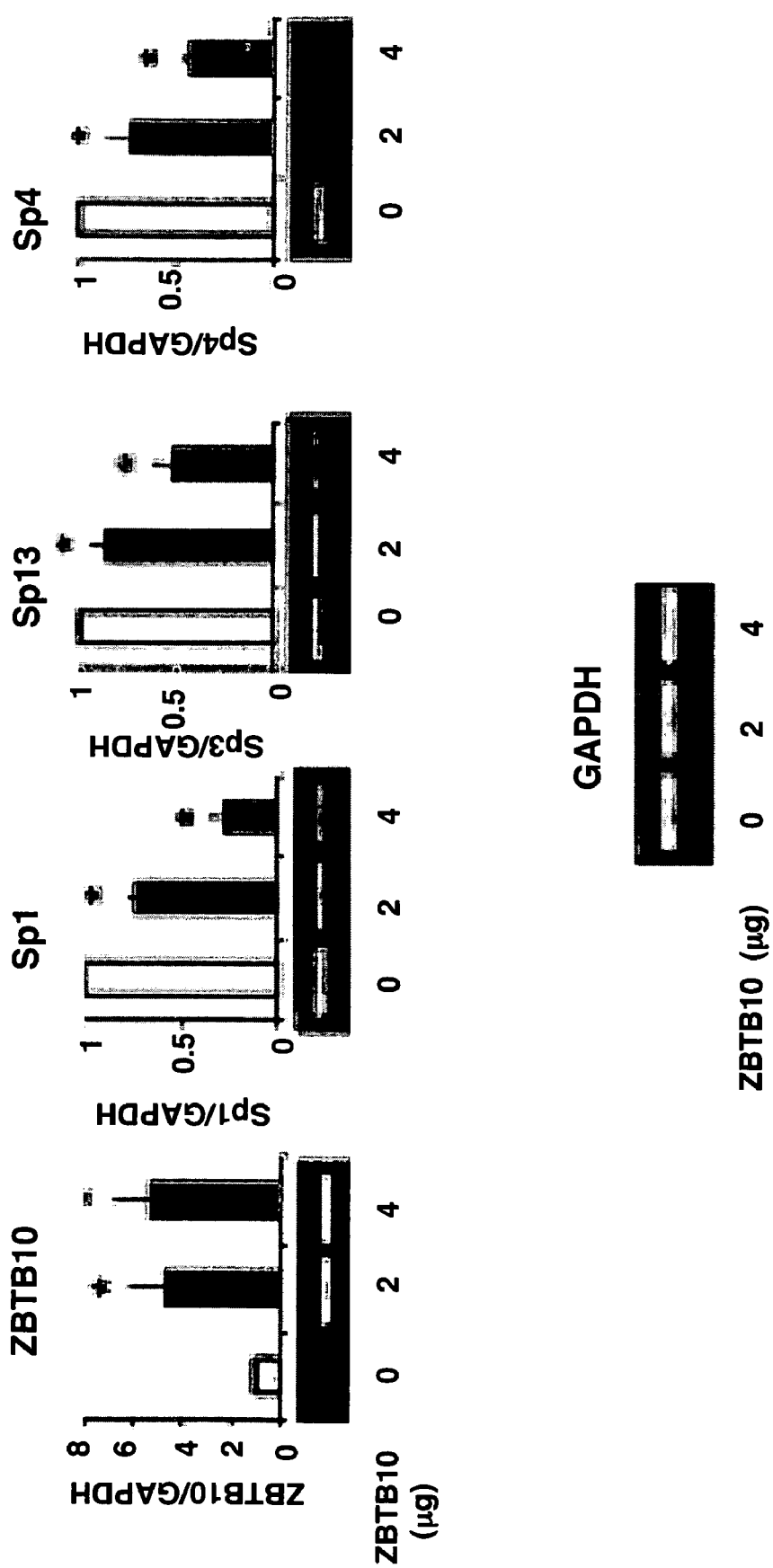
FIGS. 4A-4C illustrate the effects of ZBTB10 on expression of Sp proteins and Sp-dependent angiogenic and survival genes.
Figure 4B:
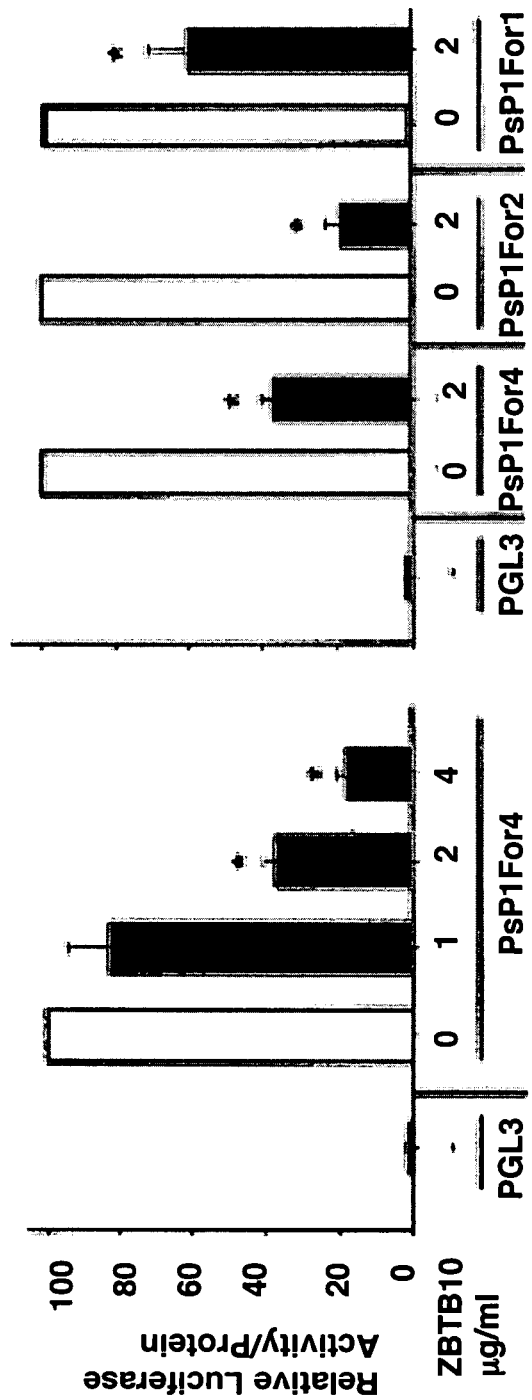
Figure 4C:
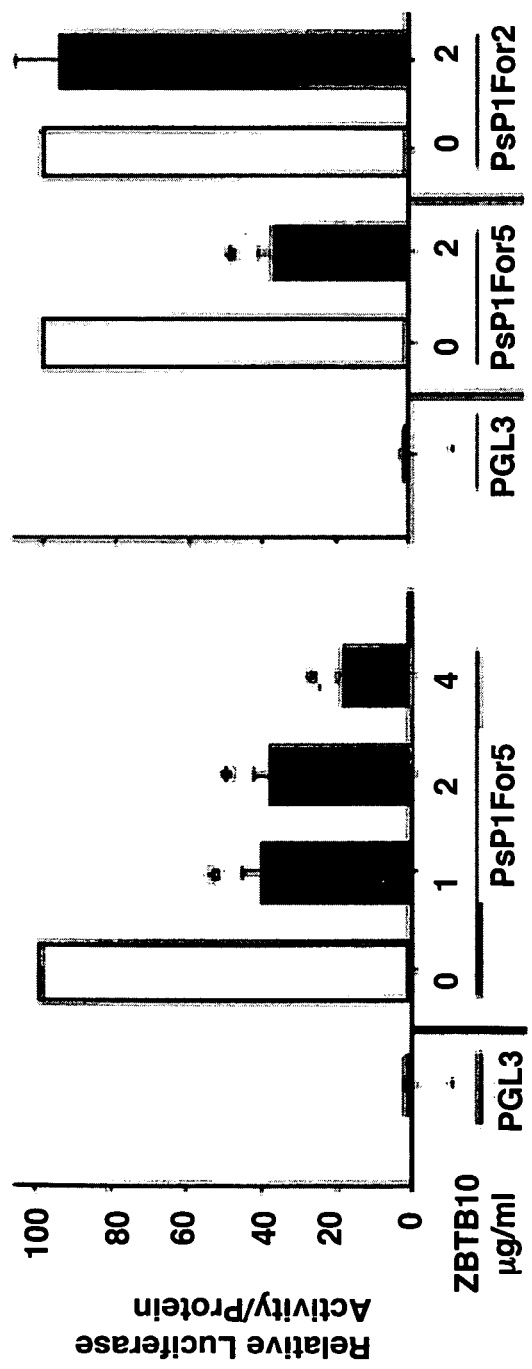

Since miR-27a regulates ZBTB10 which suppresses Sp-dependent gastrin promoter activation (29), the direct effects of ZBTB10 by overexpressing this gene in MDA-MB-231 cells was examined. FIG. 4A shows that in MDA-MB-231 cells transfected with a ZBTB10 expression plasmid, there were increased ZBTB10 mRNA levels which was accompanied by decreased Sp1, Sp3 and Sp4 mRNA levels. FIGS. 4B-4C show the effects of ZBTB10 on Sp1 and Sp3 promoter constructs. This demonstrates that overexpression of ZBTB10 decreases transactivation in MDA-MB-231 cells transfected with pSp1For4. Similar decreases occur after transfection with the deletion constructs pSp1For4, pSp1For2 and pSp1For1. ZBTB10 also decreased transactivation in MDA-MB-231 cells transfected pSp3For5 (FIG. 4C). This was comparable to the effects of as-miR-27a using these same constructs (FIGS. 2C-2D). However, ZBTB10 did not decrease luciferase activity in cells transfected with pSp3For2 which differs from the effects of as-miR-27a on this same construct suggesting that as-miR-27a may repress Sp3 expression by activation of ZBTB10 and possibly other proteins that do not act through GC-rich motifs.

EXAMPLE 6

Figure 5C:
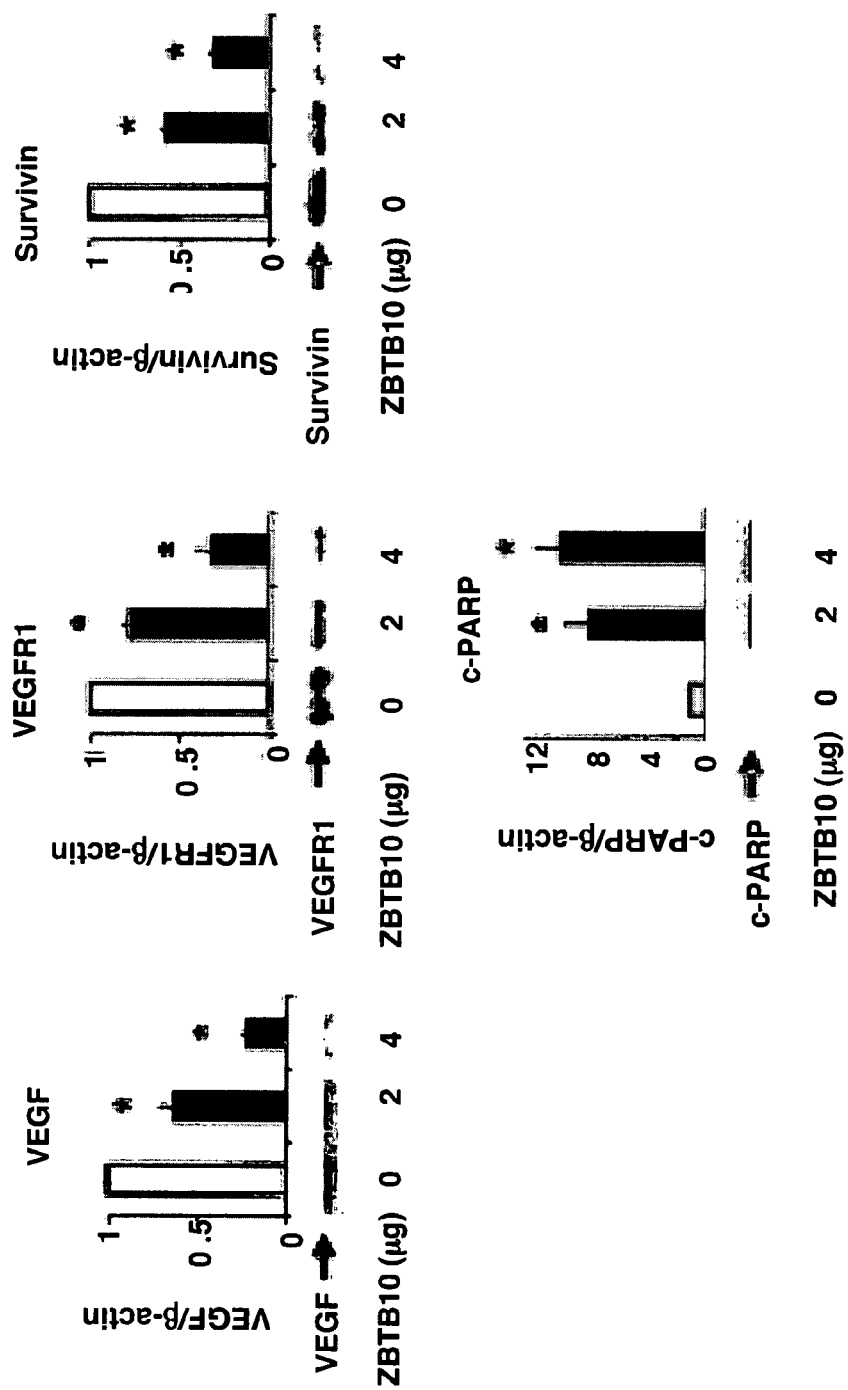

Effects of ZBTB10 Expression on SP Proteins, Sp-Dependent Genes/Proteins and Apoptosis The effects of ZBTB10 expression on Sp proteins and on Sp-dependent angiogenic and survival genes/proteins were examined. FIG. 5A shows that ZBTB10 expression in MDA-MB-231 cells significantly decreased expression of Sp1, Sp3 and Sp4 proteins. This was accompanied by decreased expression of VEGF, VEGFR1 and survivin mRNA levels (FIG. 5B) and their corresponding proteins (FIG. 5C). Decreased expression of these proteins was accompanied by activation of apoptosis as demonstrated by caspase-dependent PARP cleavage. As-miR-27a and overexpression of ZBTB10 gave complementary results in MDA-MB-231 cells and decreased expression of Sp proteins and promoters and Sp-dependent genes.

EXAMPLE 7

Antisense miR-27a Induces G2/M Arrest in MDA-MB-231 Cells

Figure 6C:
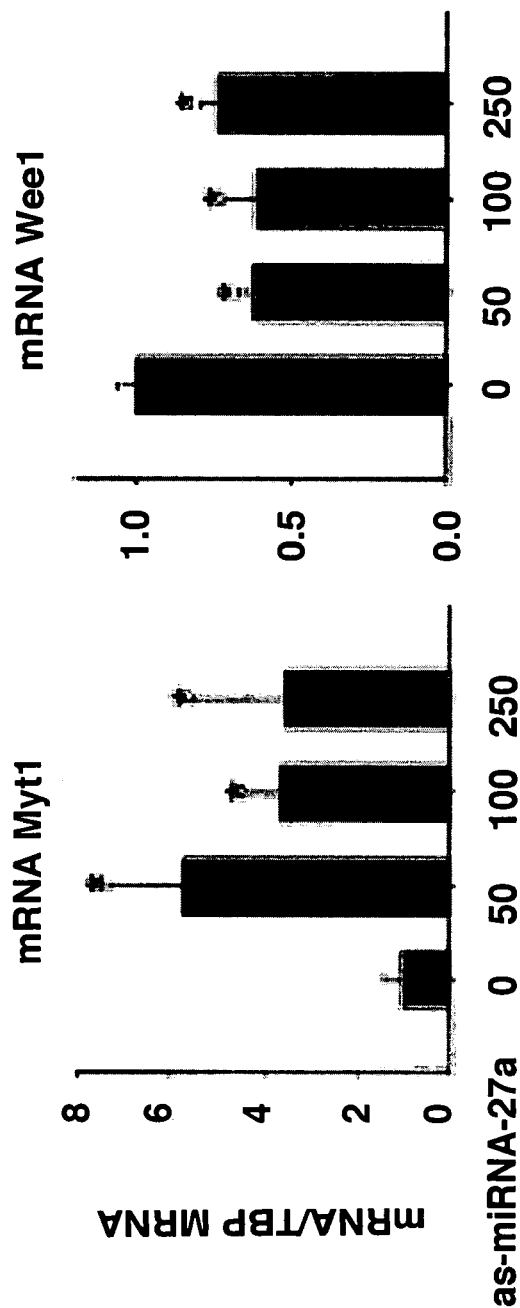
Figure 6D:
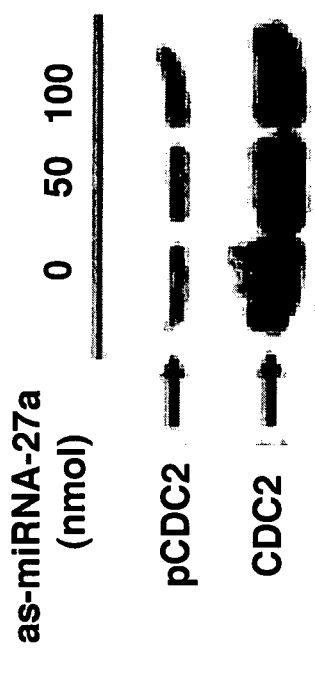

The effects of transfected as-miR-27a and ZBTB10 expression plasmid on MDA-MB-231 cell cycle progression were determined by FACS analysis. FIG. 6A shows that the percentage of MDA-MB-231 cells in G0/G1, S and G2/M phases of the cell cycle were 55, 29 and 16%, respectively. Transfection with 25, 100 or 250 ng/ml as-miR-27a significantly decreased the percentage of cells in S phase and increased the percentage in G2/M phase with minimal effects on the percentage of cells in G0/G1. In contrast, ZBTB10 overexpression (1.0-4.0 μg/ml) resulted in an increase of cells in G0/G1 and a decrease of cells in S phase (FIG. 6B). This is comparable to results of RNA interference with Sp1 knockdown in MCF-7 cells which also resulted in inhibition of G0/G1 to S phase progression (25). The differences between as-miR-27a and ZBTB10 overexpression on percentage distribution of MDA-MB-231 cells in different phases of the cell cycle suggests that miR-27a also may modulate expression of genes/proteins that inhibit cells from progressing past G2/M phase. The list of possible targets for miR-27a (38-41) includes two genes, Wee-1 and Myt-1 that inhibit cdc2 and the cdc2/cyclin B-mediated G2 to M phase progression. FIG. 6C demonstrates that as-miR-27a also increases Myt-1, but not Wee-1, mRNA levels. As-miR-27a also enhanced phosphorylation of cdc2 as determined using an antibody against phosphotyrosine-15 of cdc2 which is the inactive phospho-cdc2 (FIG. 6D). This accounts for the effects of as-miR-27a on blocking cells at G2/M in the cell cycle and show that in addition to ZBTB10, Myt-1 also is regulated by miR-27a and this contributes to the proliferative phenotype of these ER-negative breast cancer cells. These results demonstrate that miR-27a is an oncogenic microRNA through suppression of ZBTB10 and Myt-1 and that transfection of as-miR-27a induces multiple growth inhibitory, apoptotic and antiangiogenic genes and pathways in MDA-MB-231 cells. It also was demonstrated that expression of miR-27a in other cancer cell lines, e.g., prostate, colon, pancreas, and bladder, and agents such as betulinic acid and tolfenamic acid that decrease expression of Sp proteins and Sp-dependent genes also may act through downregulation of miR-27a.

EXAMPLE 8

Effects of Betulinic Acid on miR-27a Expression

Northern blot demonstrates that miR-27a is expressed in various cancers, such as breast, colon, pancreatic, and kidney (FIG. 7A). As shown in FIG. 7B, betulinic acid decreased levels of miR-27a RNA in these cancer cells. Other compounds such as tolfenamic acid and methyl-2-cyano-3,11-dioxo-18β-olean-1,12-dien-30-oate (CDODA-Me) also decrease the levels of miR-27a RNA in these and other cancer cells (23,42,43).

EXAMPLE 9

Xenograft Studies in Athymic Mice

Mice were used in accordance with institutional guidelines when they were 8-12 wk old. To produce tumors, RKO cells were harvested from subconfluent cultures by a brief exposure to 0.25% trypsin and 0.02% EDTA and only suspensions consisting of single cells with >90% viability were used for the injections. A xenograft was established by s.c. injection of the cells ($5 \times 10^6$) into the flanks of individual mice and, after 6 days, mice were randomized into two groups of 5 mice per group and dosed by oral gavage in corn oil or 15 mg/kg/d B-CDODA-Me 5 days a week for 22 days. The mice were weighed, and tumor size was measured every third day with calipers to permit calculation of tumor volumes: $V=LW^2/2$, where L and W were length and width, respectively. Final tumors weights were determined at the end of the dosing regimen. Tumor tissues and selected body organs (liver and kidney) were either stored in RNAlater solution (per manufacture's recommendations) for later microRNA analysis, snap frozen and stored at $-80°$ C., or fixed in 10% formalin and embedded in paraffin.

Figure 8A:
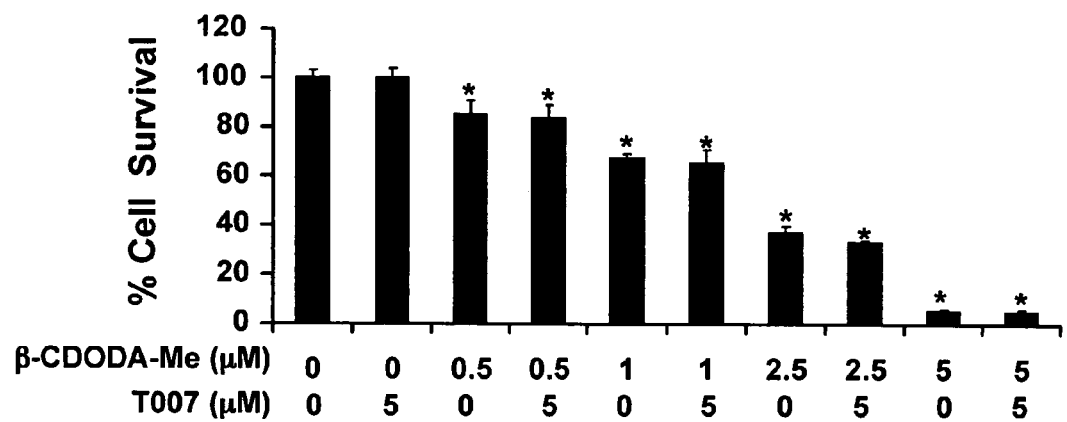
Figure 8B:
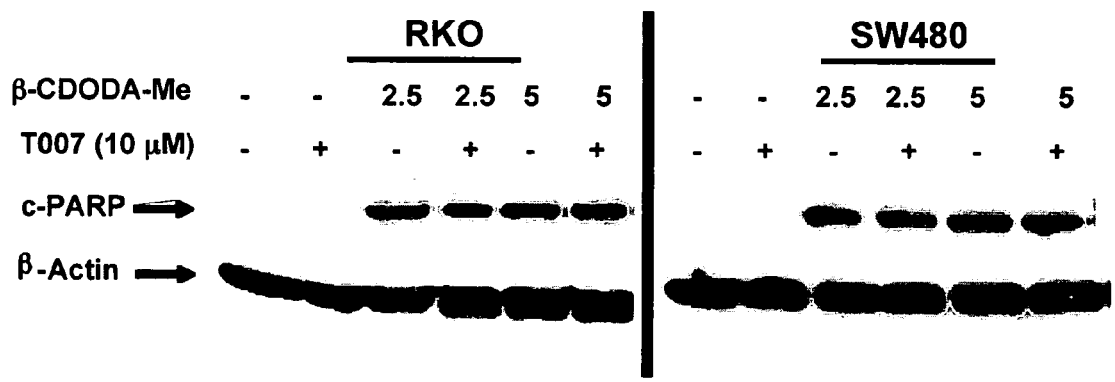

Results

β-CDODA-Me is a PPARγ agonist in colon cancer cell lines. Although β-CDODA-Me decreased proliferation (FIG. 8A) and induced apoptosis (FIG. 8B) in RKO and SW480 cells, these responses were not affected after cotreatment with the PPARγ agonist T007, and receptor-independent effects have been observed for other PPAR agonists in colon cancer cells. Studies with tolfenamic acid and the structurally-related triterpenoid betulinic acid show that many of the growth inhibitory and proapoptotic responses in pancreatic and prostate cancer cells are due to decreased expression of Sp proteins. Results summarized in FIG. 8C show that β-CDODA-Me induced a concentration- and time-dependent decrease in Sp1, Sp3 and Sp4 proteins in RKO and SW480 cells and, in RKO cells, decreases were observed with concentrations lower than 1.0 μM after treatment for 48 hr. The role of PPARγ and activation of proteasomes in mediating the effects of β-CDODA-Me on Sp protein expression was also investigated in RKO cells (FIG. 8D). β-CDODA-Me-induced downregulation of Sp1, Sp3 and Sp4 in RKO cells was not affected after cotreatment with the PPARγ antagonist T007 or the proteasome inhibitor lactacystin, and similar results were observed in SW480 cells. The proteasome inhibitor MG132 also did not block Sp protein downregulation in RKO and SW480 cells treated with β-CDODA-Me, suggesting that β-CDODA-Me-dependent Sp protein degradation is proteasome-independent.

Figure 9A:
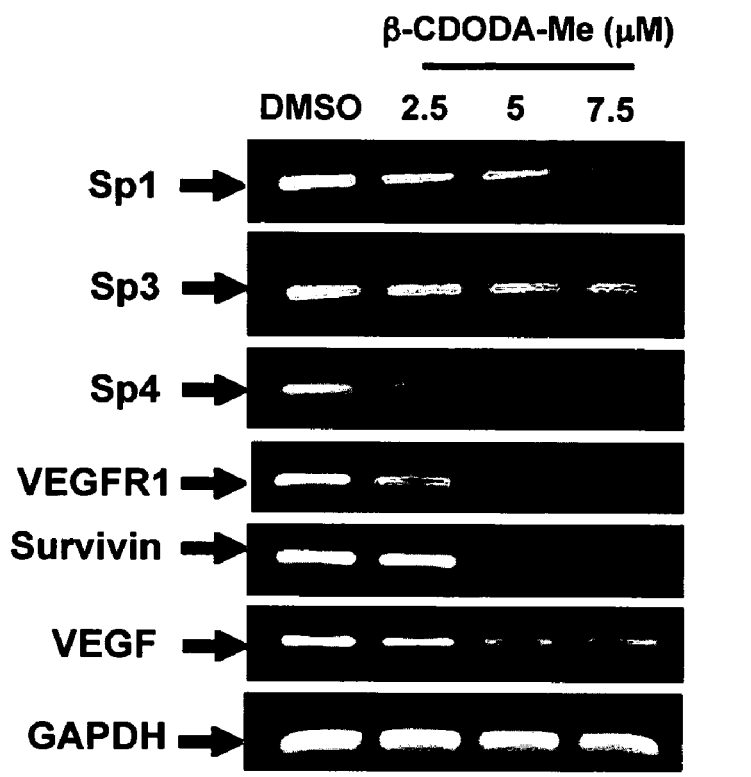
FIGS. 9A-9D (F2 of paper) show the effects of β-CDODA-Me on Sp and Sp-dependent expression. β-CDODA-Me decreases expression of Sp1, Sp3 and Sp4 proteins (FIG. 9A) and expression of angiogenic/survival genes (A) and proteins (FIG. 9B). RKO cells were treated with different concentrations of β-CDODA-Me and after 24 hr, mRNA and protein were extracted and analyzed by semi-quantitative RT-PCR and Western blots, respectively. β-CDODA-Me decreases Sp1 (FIG. 9C) and Sp3 (FIG. 9D) promoter activity. RKO cells were transfected with various constructs, treated with different concentrations of β-CDODA-Me, and luciferase activity was determined. Results are expressed as means±SE for three replicate determinations for each treatment group and significantly (p<0.05) decreased activity is indicated by an asterisk.
Figure 9B:
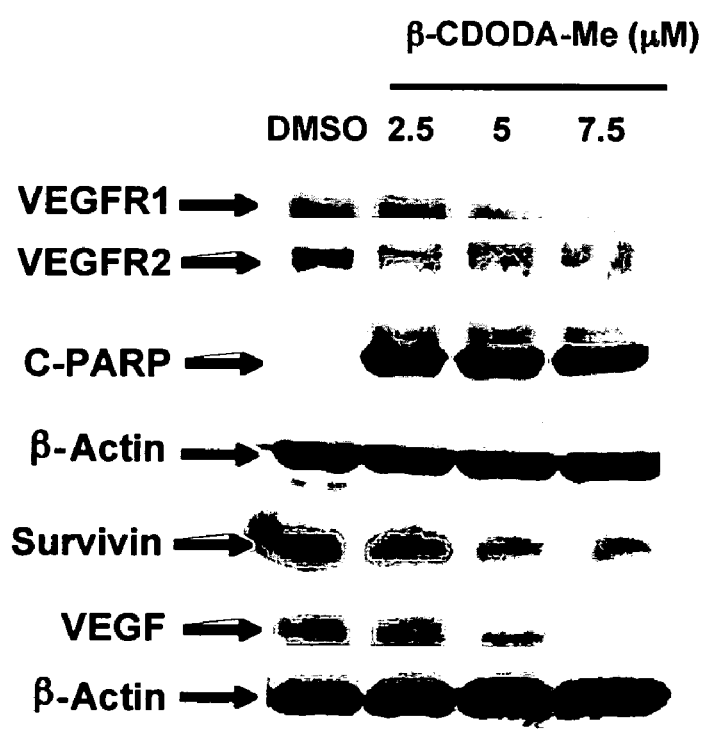
Figure 9C:
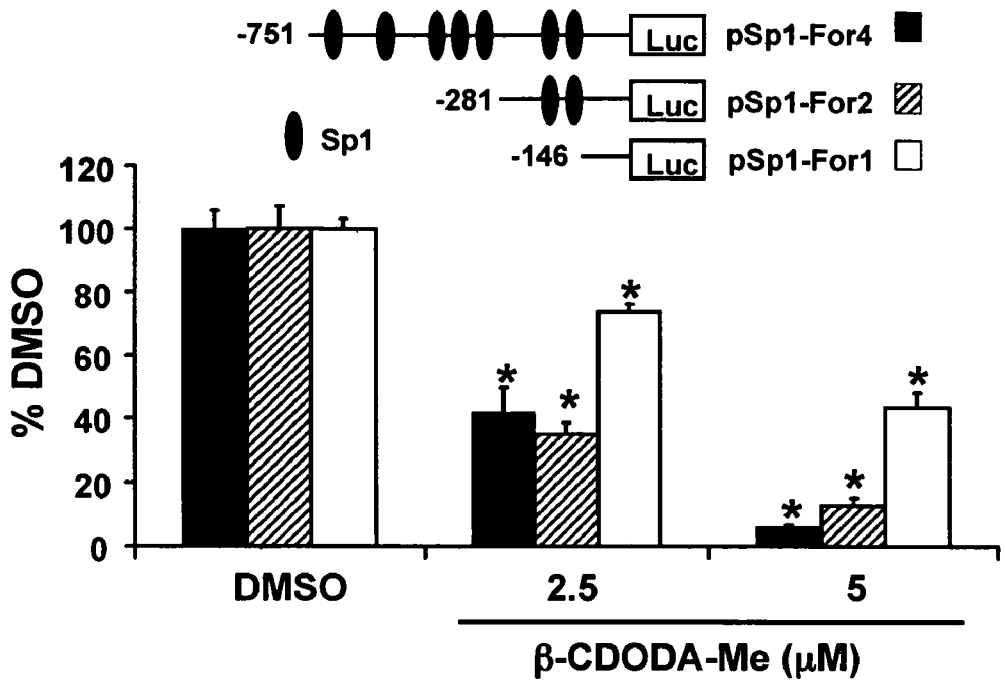
Figure 9D:
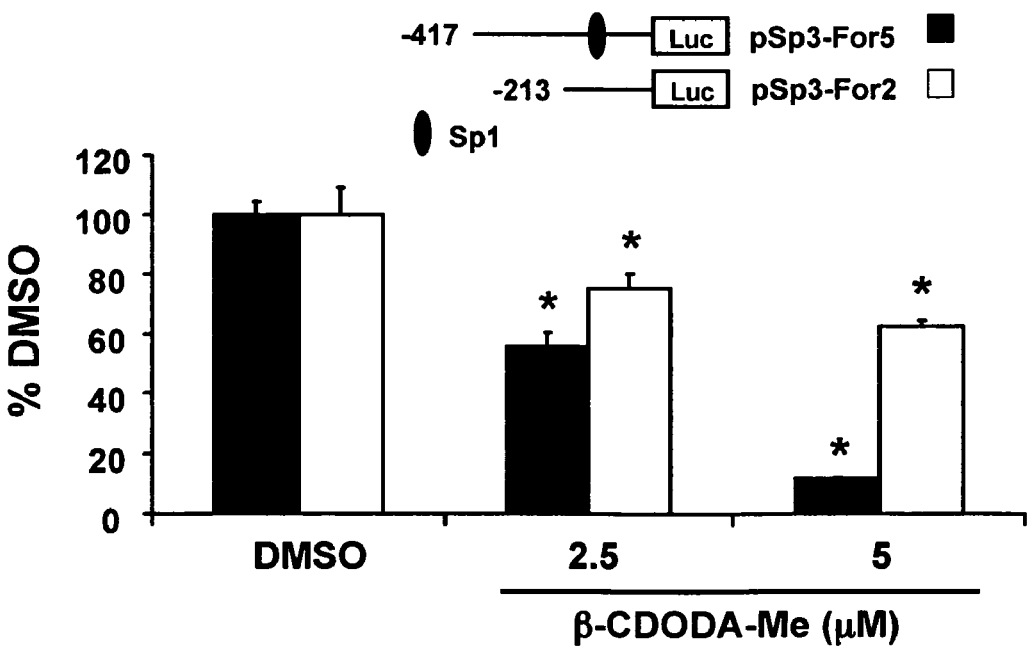

Using RKO cells as a model, β-CDODA-Me induced caspase-dependent PARP cleavage and decreased expression of at least three Sp-dependent proteins including survivin, VEGFR1 (Flt-1), and VEGF (FIG. 9A). FIG. 9B shows that β-CDODA-Me also decreased expression of Sp1, Sp3 and Sp4 mRNA levels after treatment for 24 hr, and similar effects were observed for mRNA levels of the Sp-dependent genes VEGFR1, VEGF and survivin (FIG. 9B). Both the Sp1 and Sp3 promoters contain GC-rich sites, and FIG. 9C shows that β-CDODA-Me decreased luciferase activity in RKO cells transfected with pSp1For4, pSp1For2 and pSp1For1 constructs which contain the −751 to −20, −281 to −20, and −146 to −20 regions (respectively) of the Sp1 gene promoter. Similarly, β-CDODA-Me also decreased luciferase activity in RKO cells transfected with pSp3For5 and pSp3For2 constructs that contain the 417 to −38 and −213 to −38 regions (respectively) of the Sp3 gene promoter. These results demonstrate that β-CDODA-Me decreases Sp1, Sp3 and Sp4 transcription.

Figure 10A:
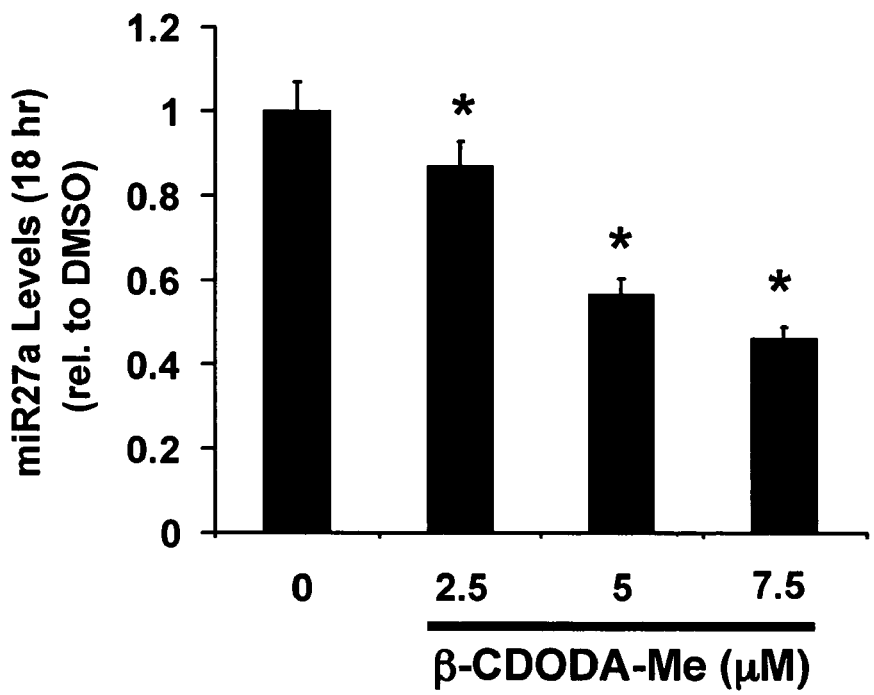
Figure 10B:
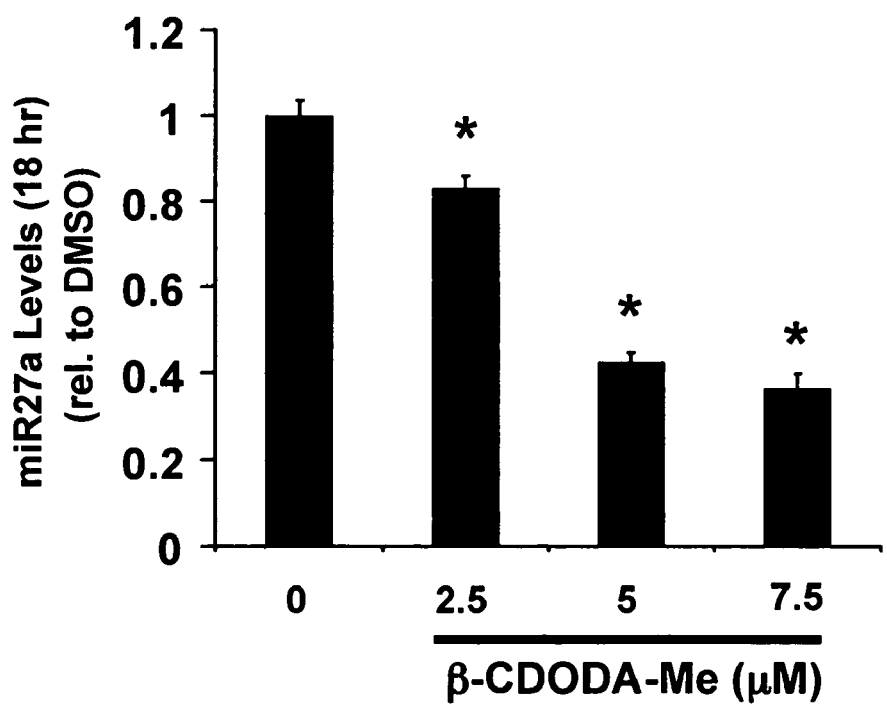
Figure 10C:
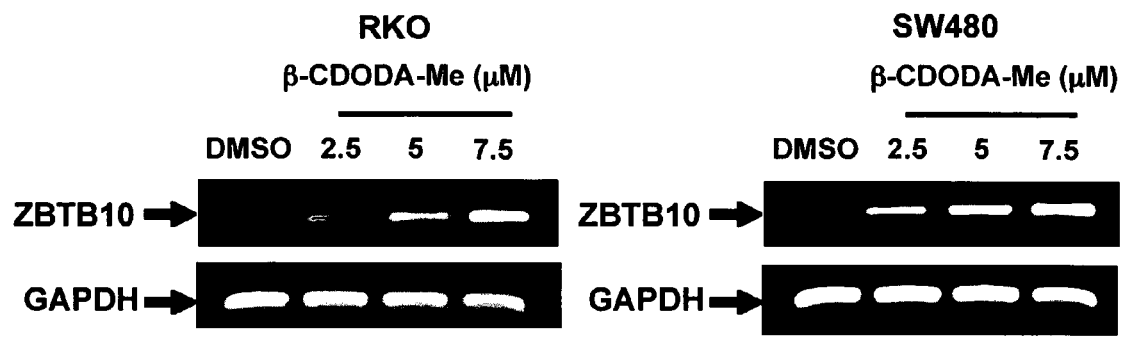
Figure 10D:
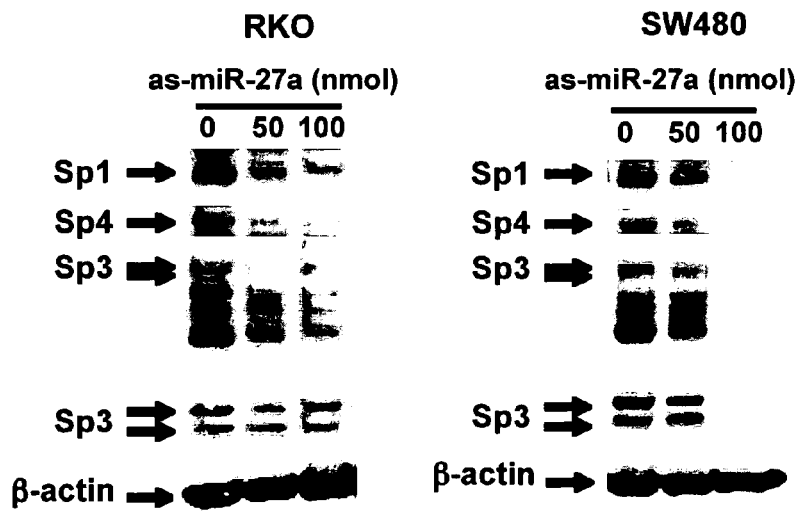

It was recently reported that microRNA-27a (miR-27a) suppresses ZBTB10 mRNA levels in breast cancer cells and treatment with antisense miR-27a (as-miR-27a) increases expression of ZBTB10 and decreases expression of Sp mRNA and proteins. Results illustrated in FIGS. 10A and 10B show that β-CDODA-Me decreased miR-27a in RKO and SW480 cells as determined by quantitative real time PCR and similar results were observed in Northern blot analysis. In addition, treatment of RKO or SW480 cells with β-CDODA-Me also induced ZBTB10 levels (FIG. 10C). Thus, the effects of β-CDODA-Me on miR-27a and ZBTB10 expression in colon cancer cells are identical to those observed in breast cancer cells transfected with as-miR-27a which also increases ZBTB10 and decreases Sp protein expression. Results in FIG. 10D confirm that as-miR-27 also decreased expression of Sp1, Sp3 and Sp4 protein levels in RKO and SW480 colon cancer cells.

Figure 11A:
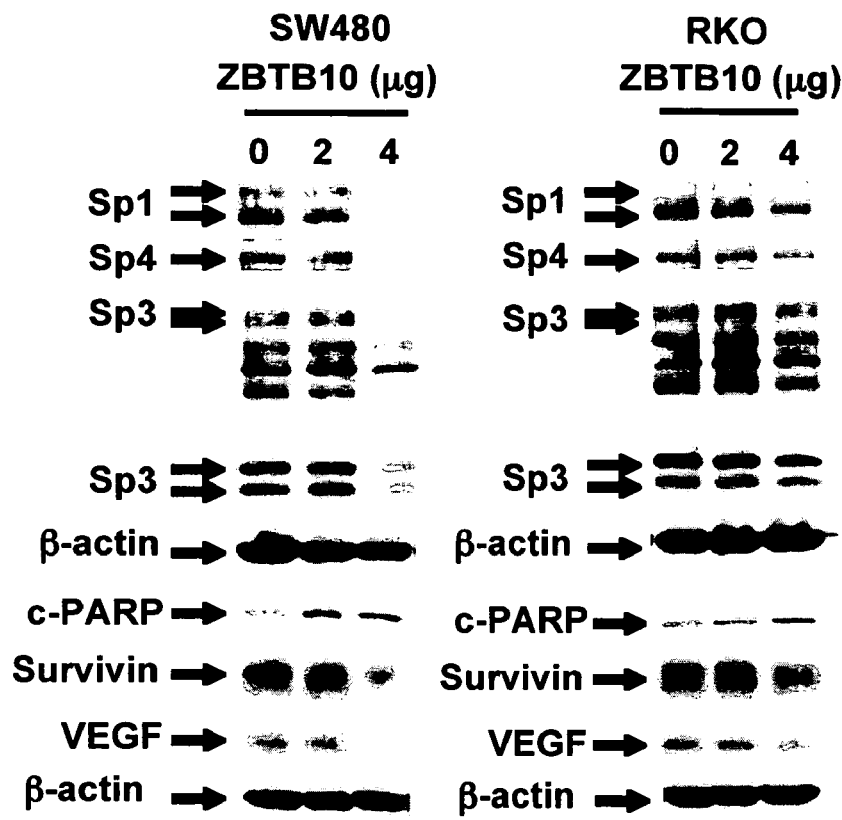
FIGS. 11A-11D show that ZBTB10 decreases expression of Sp proteins and Sp-dependent angiogenic and survival genes. ZBTB10 expression decreases expression of Sp and angiogenic/survival proteins (FIG. 11A) and mRNA (FIG. 11B). RKO and SW480 cells were transfected with ZBTB10 expression plasmid and after 24 hr, protein and mRNA were extracted and analyzed by Western blots and semi-quantitative RT-PCR, respectively. ZBTB10 expression decreases Sp1 and Sp3 (FIG. 11C) and VEGF and survivin (FIG. 11D) promoter activity. RKO cells were transfected with various constructs and ZBTB10 expression plasmid, and luciferase activity was determined. Results are expressed as means±SE for three replicate determinations for each treatment group and significantly (p<0.05) decreased activity is indicated by an asterisk.
Figure 11B:
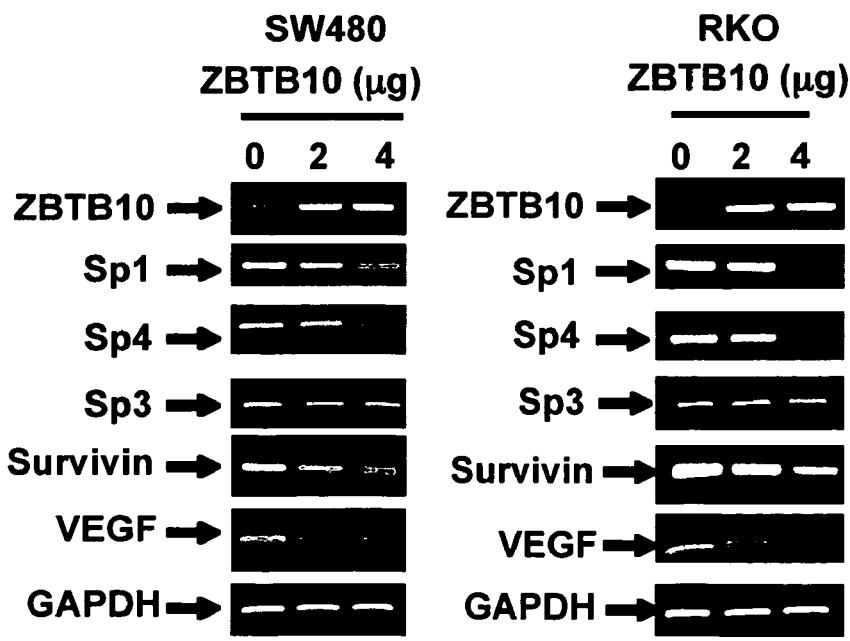
Figure 11C:
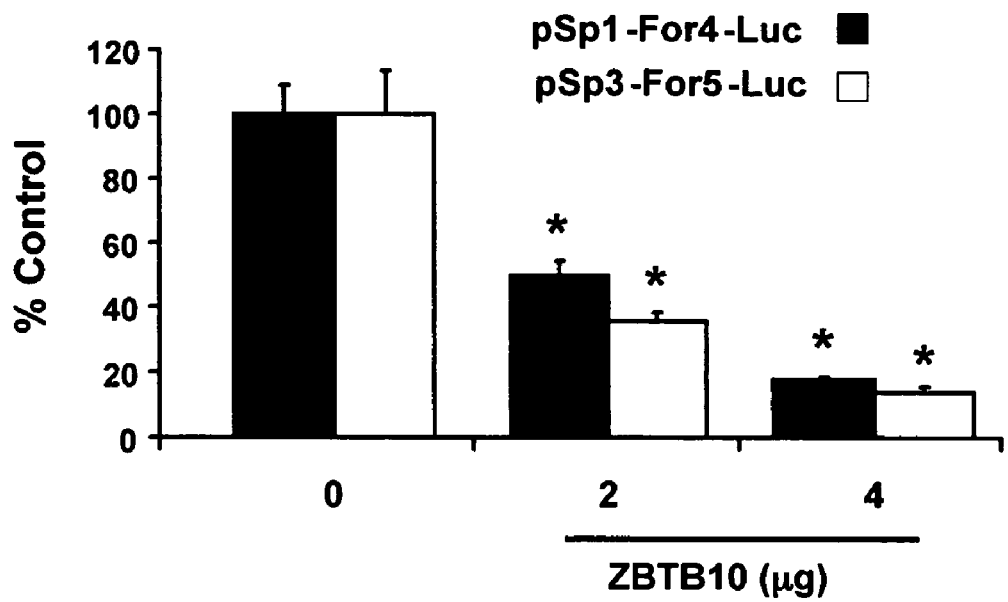
Figure 11D:
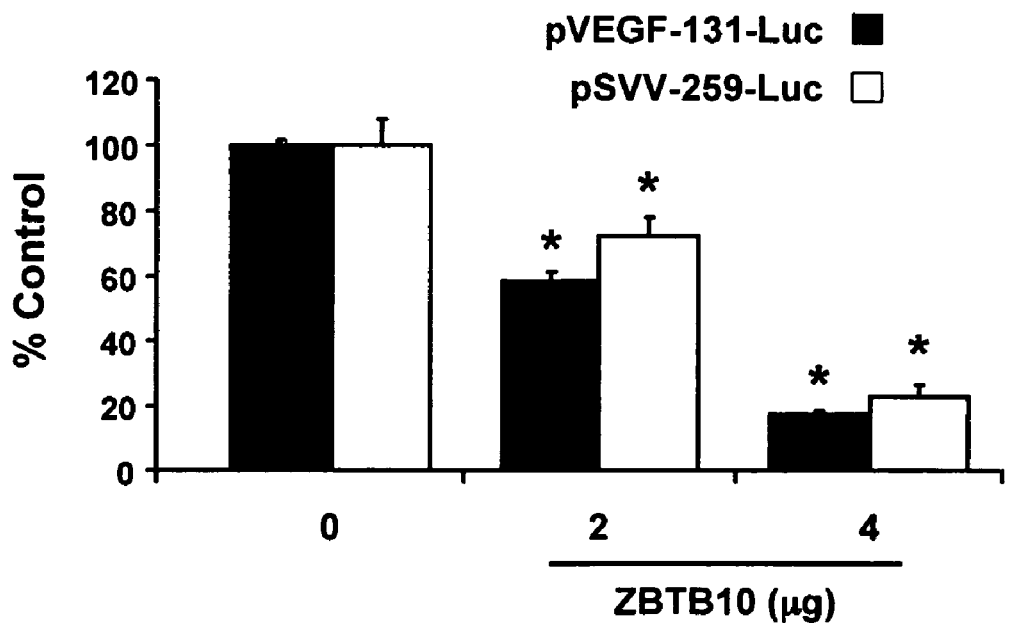

The direct effects of ZBTB10 as a "putative" Sp repressor were further investigated in colon cancer cells transfected with ZBTB10 expression plasmid. Transfection of SW480 and RKO cells with 2 or 4 μg ZBTB10 expression plasmid decreased Sp1, Sp3 and Sp4 mRNA levels and decreased the Sp-dependent VEGF and survivin mRNA levels (FIG. 11A). These responses were more pronounced in RKO cells and this may be due, in part, to higher basal expression of ZBTB10 in SW480 than in RKO cells. These differences between the two cell lines were less apparent for the effects of ZBTB10 on Sp and Sp-dependent proteins (FIG. 11B). ZBTB10 overexpression decreased levels of Sp1, Sp3 and Sp4 proteins, survivin and VEGF and induced PARP cleavage in these cells. The effects of ZBTB10 on luciferase activity in RKO cells transfected with constructs containing GC-rich Sp1 and Sp3 gene promoter inserts (FIG. 11C) and VEGF and survivin promoter inserts (FIG. 11D) complemented the effects of ZBTB10 on their respective mRNAs and proteins (FIGS. 11A and 11B). Luciferase activity was decreased in RKO cells transfected with all constructs and similar results were observed in SW480 cells.

Figure 12A:
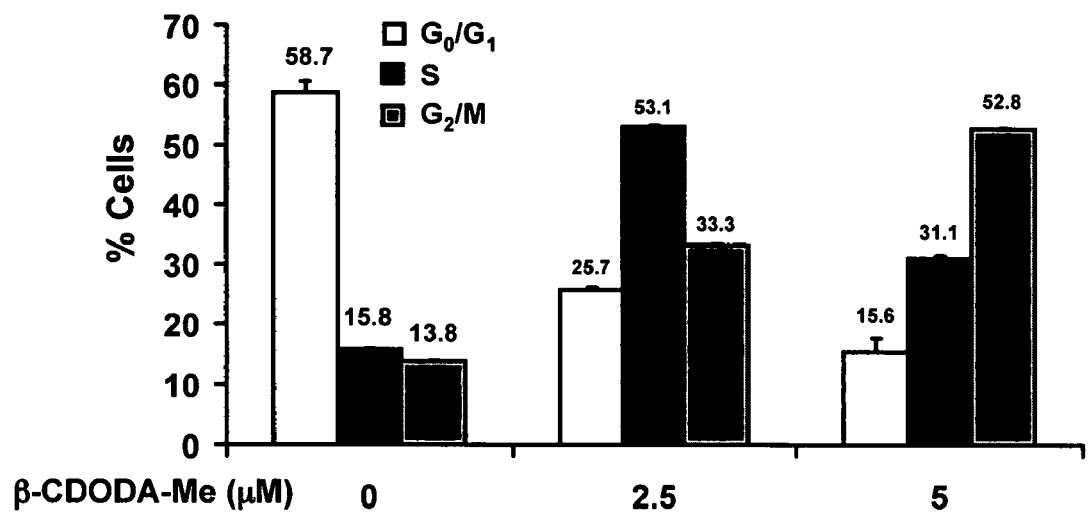
FIGS. 12A-12B shows modulation of cell cycle progression. Effects of β-CDODA-Me. SW480 (FIG. 12A) and RKO (FIG. 12B) cells were treated for 24 hr with DMSO(O), 2.5 and 5.0 μM β-CDODA-Me, and analyzed by FACS analysis.
Figure 12B:
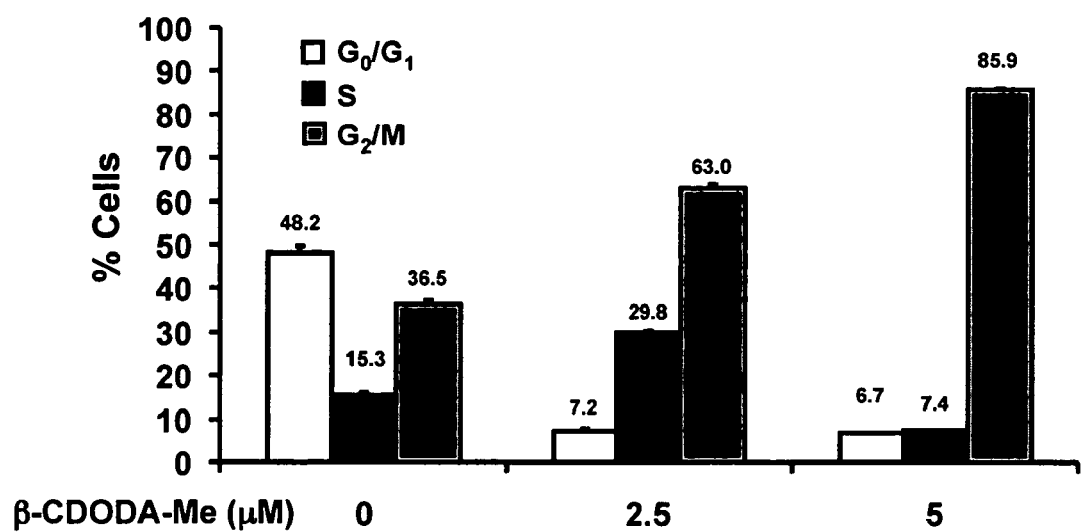

FIGS. 12A and 12B summarizes the effects of β-CDODA-Me on distribution of RKO and SW480 cells in $G_0/G_1$, S and $G_2/M$ phases of the cell cycle. Compared to treatment with DMSO, β-CDODA-Me induced a concentration-dependent decrease in the percentage of cells in $G_0/G_1$ and an increase of cells in $G_2/M$. The percentage of cells in S phase increased and then decreased after treatment with 2.5 and 5.0 µM β-CDODA-Me, respectively; however, the dominant effects of β-CDODA-Me were associated with a block in progression through $G_2/M$. The potential role of Sp protein degradation on mediating the effects of β-CDODA-Me on distribution of cells in different phases of the cell cycle was determined by RNA interference using a combination of small inhibitory RNAs for Sp1 (iSp1), Sp3 (iSp3) and Sp4 (iSp4) as previously described for knockdown of these proteins in other cancer cell lines. Transfection of SW480 and RKO with iSp1/iSp3/iSp4 (combined; iSp) significantly decreased expression of all three proteins (least efficiency observed for Sp4) and, compared to the results for iLamin (non-specific RNA), Sp knockdown caused a significant $G_0/G_1$ to S phase arrest. These results are comparable to previous studies in MCF-7 breast cancer cells transfected with iSp1; however, the data were in contrast to the effects of β-CDODA-Me which induced a $G_2/M$ arrest in both RKO and SW480 cells. Since β-CDODA-Me and as-miR-27a induced similar responses in colon cancer cells, the effects of as-miR-27a on distribution of RKO and SW480 cells in $G_0/G_1$, S and $G_2/M$ phases were also examined. The results (FIG. 12D) demonstrate that like β-CDODA-Me, as-miR-27a induced a $G_2/M$ arrest in colon cancer cells. Transfection of as-miR-27a (100 nM RKO; 200 nM SW480) increased accumulation of cells in $G_2/M$ and this was accompanied by a decrease in percentage of cells in S (SW480) and $G_0/G_1$ (RKO) phases. However, the magnitude of the $G_2/M$ arrest observed in colon cancer cells transfected with as-miR-27a was lower than observed for β-CDODA-Me, suggesting that the compound-induced response may also be due to other factors.

Figure 13A:
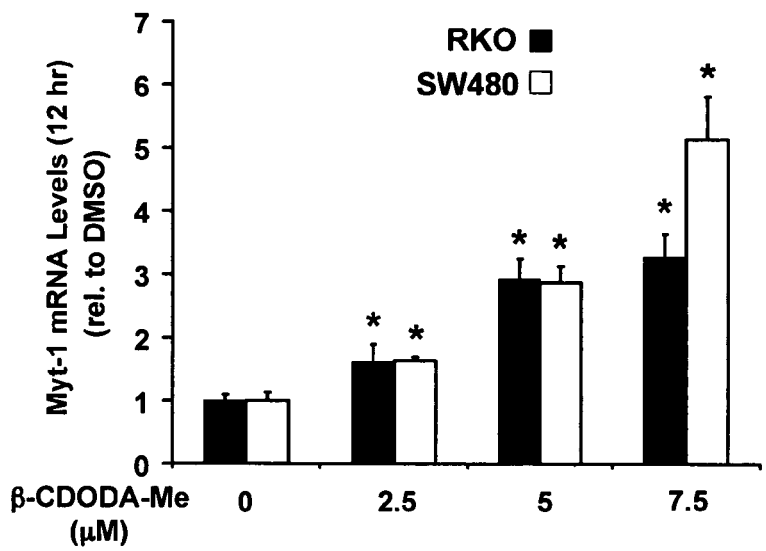
FIGS. 13A-13C show the in vitro and in vivo effects of β-CDODA-Me on $G_2/M$ arrest and inhibition of tumor growth. Effects of β-CDODA-Me (FIG. 13A, 13B) and as-miR-27a (FIG. 13C) on Myt-1 and cdc2 phosphorylation. Colon cancer cells were treated with different amounts of β-CDODA-Me or as-miR-27a for the indicated times, and Myt-1 expression and cdc2 phosphorylation were determined by real time PCR or Western blots, respectively. The effects of as-miR-27a on Myt-1 mRNA expression in RKO cells was similar to SW480 cells, and as-miR-27a also increased cdc2 expression as described (7).
Figure 13B:
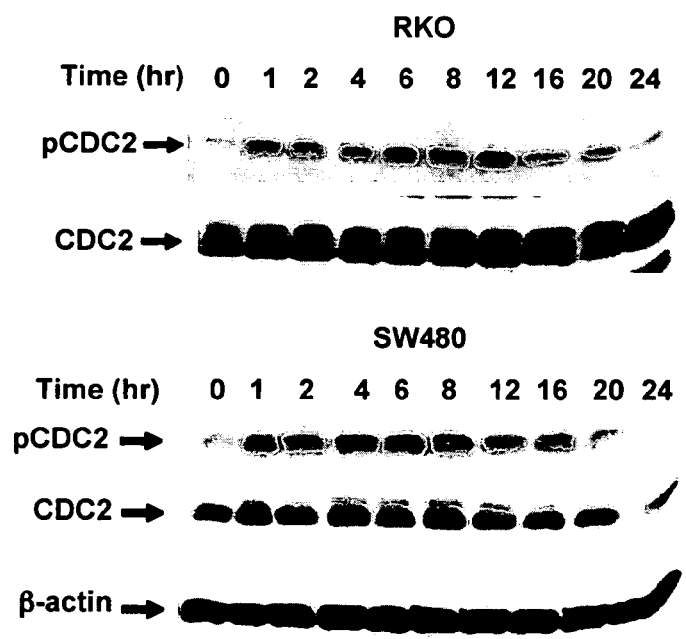
Figure 13C:
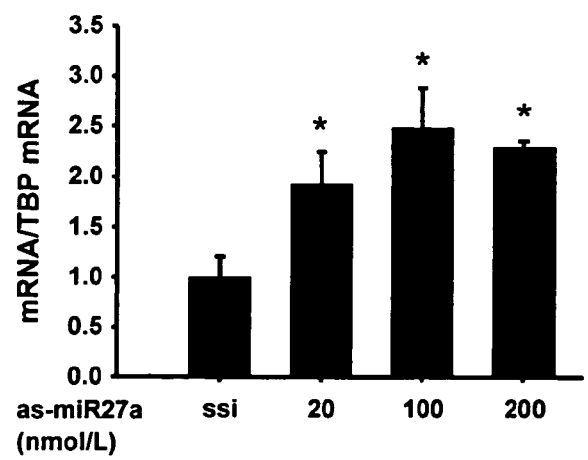
Figure 13D:
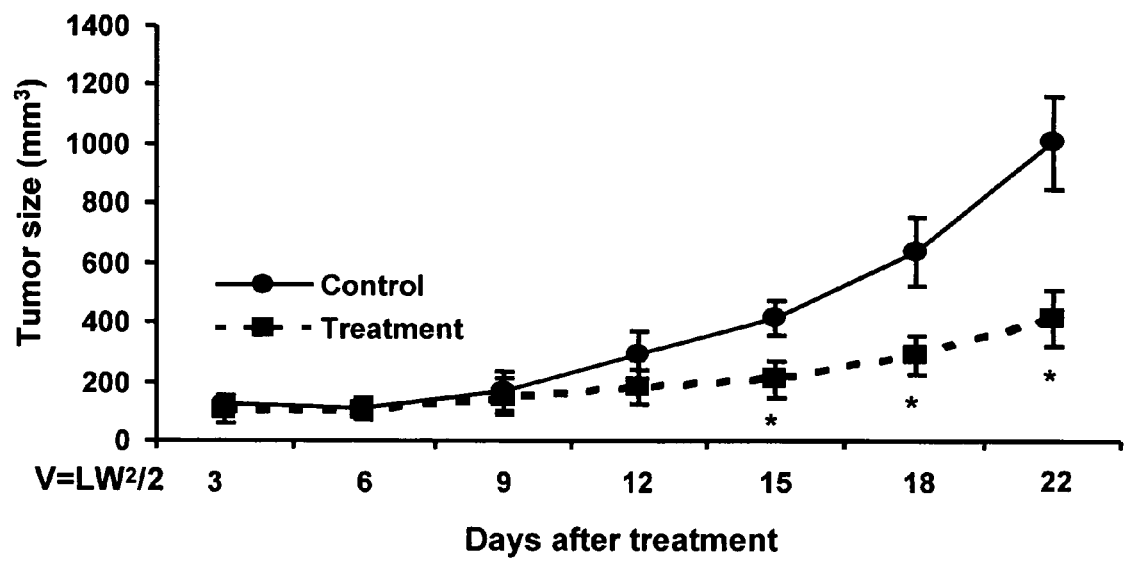
FIGS. 13D-13F: β-CDODA-Me inhibit tumor growth (volume) (FIG. 13D), weight (FIG. 13E) and miR-27a expression (FIG. 13F) in a mouse xenograft model. Nude mice bearing RKO cells as xenografts were treated with corn oil (solvent control) or β-CDODA-Me (15 mg/kg/d), and tumor volumes, tumor weights, and miR-27a expression were determined. Results are expressed as means±SE for replicate (at least three or more) determinations for each treatment group, and significantly (p<0.05) decreased tumor volume or weight is indicated by an asterisk.
Figure 13E:
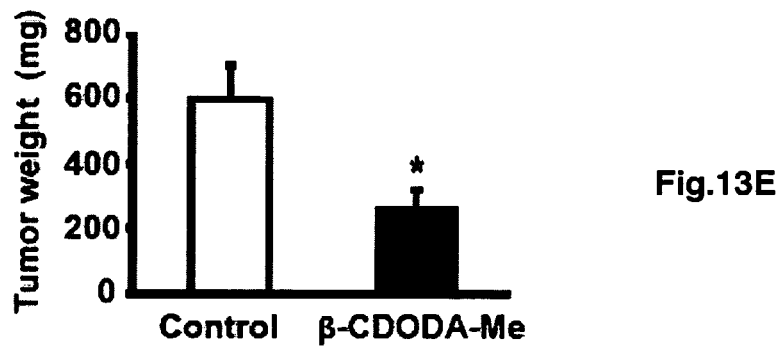
Figure 13F:
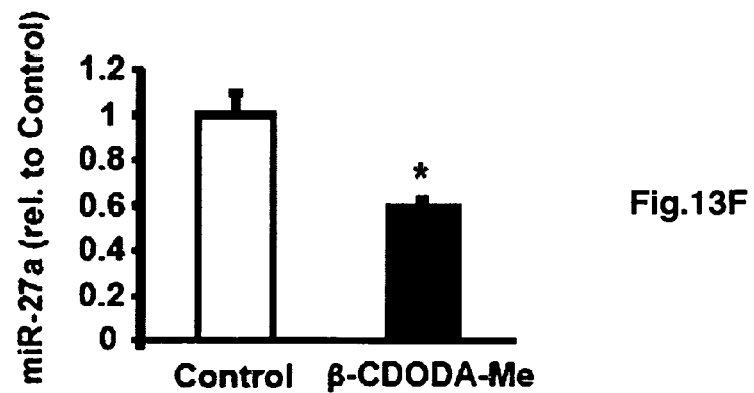

As-miR-27a also arrests MDA-MB-231 breast cancer cells in $G_2/M$ phase and this is due to upregulation of Myt-1 which is a target for miR-27a and catalyzes phosphorylation of cdc2 to inhibit progression through the $G_2/M$ checkpoint enzyme. FIG. 13A shows that β-CDODA-Me induced Myt-1 mRNA expression in RKO and SW480 cells, and this was accompanied by the time-dependent induction of cdc2 phosphorylation (FIG. 13B) as previously described in breast cancer cells transfected with as-miR-27a. Myt-1 and Wee-1 are potential miR-27a targets that inactivate cdc2; however, β-CDODA-Me and as-miR-27a induced Myt-1 (FIGS. 13A and 13C) but did not affect Wee-1 expression in SW480 or RKO cells. The in vivo activity of β-CDODA-Me as an inhibitor of tumor growth in athymic nude mice bearing RKO cells as xenografts was also investigated. β-CDODA-Me (15 mg/kg/d) inhibited tumor growth and tumor weight and miR-27a expression (FIG. 13D), and this was not accompanied by any body or organ weight loss associated with toxic side effects. Thus, β-CDODA-Me, like other compounds such as tolfenamic and betulinic acids, decrease Sp protein expression; however, β-CDODA-Me acts through targeting miR-27a downregulation in colon cancer cells and tumors. This represents a novel drug-miR interaction with potential for development of new approaches for clinical treatment of colon cancer.

Discussion

Sp1 protein is overexpressed in several tumor types compared to non-tumor tissue, and Sp1 was a negative prognostic factor for cancer survival. For example, Sp1 is overexpressed in human gastric tumors compared to non-tumor tissue and overexpression of this protein in tumors is a predictor for a poor prognosis. Sp1 is also overexpressed in malignant human fibroblast cell lines and results of Sp1 overexpression or knockdown in fibroblasts and fibrosarcoma cells has established a causal linkage between Sp1 overexpression and malignant transformation.

Sp1, Sp3 and Sp4 are highly expressed in cancer cell lines, and RNA interference studies demonstrate that these transcription factors cooperatively regulate prosurvival, growth promoting, and angiogenic genes, suggesting that targeting Sp protein degradation may be a viable strategy for cancer chemotherapy.

Both betulinic acid and tolfenamic acid inhibit growth of prostate and pancreatic tumors and cells, and these effects are linked to induction of proteasome-dependent degradation of Sp1, Sp3 and Sp4 proteins which is accompanied by decreased expression of Sp-dependent genes such as survivin, VEGF and VEGFR1. However, ongoing studies with betulinic and tolfenamic acids in other cancer cell lines indicate that their effects on decreased Sp protein and mRNA levels are primarily proteasome-independent. β-CDODA-Me induced apoptosis and inhibited SW480 and RKO colon cancer cell growth and the responses were not inhibited by the PPARγ antagonist T007 or other PPARγ antagonists. β-CDODA-Me also decreased Sp1, Sp3 and Sp4 protein expression in SW480 and RKO cells, and these responses were not inhibited by T007 or proteasome inhibitors but were related to decreased Sp1, Sp3 and Sp4 transcription factors. β-CDODA-Me decreased Sp proteins and mRNA levels and also decreased protein and mRNA levels of the Sp-dependent genes VEGF, VEGFR1 and survivin. Interestingly, β-CDODA-Me decreased transactivation in colon cancer cells transfected with pSp1For1-luc and pSp3-For2-luc which do not contain GC-rich sequences, suggesting modulation of other trans-acting factors and these are currently being investigated.

The effects of β-CDODA-Me on Sp proteins and Sp-dependent genes in colon cancer cells were reminiscent of the effects of antisense miR-27a (as-miR-27a) in ER-negative MDA-MB-231 breast cancer cells. In MDA-MB-231 cells transfected with as-miR-27a, there was a parallel increase in a zinc finger transcription factor, ZBTB10, which also binds GC-rich promoter sequences and inhibits expression of Sp1, Sp3 and Sp4 and Sp-dependent genes. β-CDODA-Me decreased miR-27a and increased ZBTB10 expression in RKO and SW480 colon cancer cells. Moreover, as-miR-27a or ZBTB10 overexpression decreased Sp proteins and mRNA levels and Sp-dependent genes (e.g. survivin and VEGF) in colon cancer cells. The effects of β-CDODA-Me on distribution of RKO and SW480 cells in the $G_0/G_1$, S and $G_2/M$ phases of the cell cycle showed that the dominant effect was accumulation of cells in $G_2/M$. Decreased Sp1 expression in MCF-7 cells by RNA interference arrests cells in $G_0/G_1$ and, in colon cancer cells transfected with small inhibitory RNAs for Sp1, Sp3 and Sp4 (combined), a significant block in $G_0/G_1$ to S phase progression was observed but no effects on $G_2/M$. Similar results were observed in MDA-MB-231 breast cancer cells transfected with ZBTB10. However, transfection of MDA-MB-231 or colon cancer cells with as-miR-27a resulted in $G_2/M$ arrest, and this mimicked the effects of β-CDODA-Me. Growth arrest in colon cancer cells treated with β-CDODA-Me was greater than observed for as-miR-27a, suggesting that the compound may activate other pathways and these are currently being investigated.

Since miR-27a potentially targets both Myt-1 and Wee-1, two kinases that inhibit cdc2 and progression of cells through the $G_2$/M checkpoint, the effects of β-CDODA-Me on cdc2 and phospho-cdc2 expression was examined. β-CDODA-Me induced Myt-1 but not Wee-1 expression in both RKO and SW480 cells, and this was accompanied by phosphorylation of cdc2 in RKO and SW480 cells. As-miR-27a also induced Myt-1 and cdc2 phosphorylation in these cell lines. Thus, like as-miR-27a, β-CDODA-Me acts through decreased expression of miR-27a, resulting in enhanced expression of ZBTB10 and Myt-1 which subsequently induce downstream growth inhibitory, proapoptotic and antiangiogenic genes and pathways in colon cancer cells. These in vitro responses induced by β-CDODA-Me were complemented by the inhibition of tumor growth and tumor weight in athymic nude mice bearing RKO cells as xenografts, and miR-27a expression was also decreased in tumors from β-CDODA-Me-treated animals compared to tumors from corn oil-treated mice.

In summary, β-CDODA-Me decreases expression of Sp proteins and Sp-dependent genes and induces $G_2$/M arrest in colon cancer cells, and these responses are due to repression of miR-27a and increased expression of ZBTB10 and Myt-1. β-CDODA-Me also accompanied by decreased tumor growth and this was also accompanied by decreased miR-27a expression in the tumor and this represents one of the first in vivo examples of a drug-miR interaction. Other compounds such as betulinic and tolfenamic acids also decrease Sp proteins in prostate and pancreatic cancer cells, and there is evidence that a hydroxamic acid histone deacetylase inhibitor decreases expression of miR-27a and other miRs in SKBR3 cells. Current studies are focused on potential clinical applications of β-CDODA-Me-miR interactions for treatment of colon cancer and delineation of other pathways important for the anticancer activity of β-CDODA-Me and related compounds.

The following references are cited herein.
1. Dynan W S and Tjian R. (1983) Cell 35:79-87.
2. Dynan W S and Tjian R. (1983) Cell 32:669-680.
3. Philipsen S and Suske G. (1999) Nucleic Acids Res. 27:2991-3000.
4. Bouwman P and Philipsen S. (2002) Mol. Cell. Endocrinol. 195:27-38.
5. Black et al. (2001) J. Cell. Physiol. 188:143-160.
6. Safe S and Abdelrahim M (2005) Eur. J. Cancer 41:2438-2448.
7. Marin et al. (1997) Cell 89:619-628.
8. Bouwman et al. (2000) EMBO J. 19:655-661.
9. Gollner et al. (2001) Mech. Dev. 106:77-83.
10. Supp et al. (1996) Dev. Biol. 176-284-299.
11. Safe S and Kim K. (2004) Prog. Nucleic Acid Res. Mol. Biol. 77:1-36.
12. Wang et al. (2003) Clin. Cancer Res. (:6371-6380.
13. Yao et al. (2004) Clin. Cancer Res. 10:4109-4117.
14. Shi et al. (2001) Cancer Res. 61:4145-4154.
15. Zannetti et al. (2000) Cancer Res. 60:1546-1551.
16. Chiefari et al. (2002) 2:35.
17. Hosoi et al. (2004) Int. J. Oncol. 25:461-468.
18. Kanai (2006) Clin. Cancer Res. 12:6395-6402.
19. Lou et al. (2005) Cancer Res. 65:1007-1017.
20. Higgins et al. (2006) Biochem. Biophys. Rs. Commun. 345:292-301.
21. Abdelrahim et al. (2004) Cancer Res. 64:6740-6749.
22. Abdelrahim et al. (2007) Cancer Res. (in press).
23. Abdelrahim et al. (2006) J. Natl. Cancer Inst. 98:855-868.
24. Abdelrahim M and Safe S. (2005) Mol. Pharmacol. 68:317-329.
25. Adbelrahim et al. (2002) J. Biol. Chem. 277:28815-28822.
26. Pillai R S. (2005) RNA 11: 1753-1761.
27. Zamore P D and Haley B. (2005) Science 309:1519-1524.
28. Scott et al. (2006) Cancer Res. 66:1277-1281.
29. Tillotson L G. (1999) J. Biol. Chem. 274:8123-8128.
30. Takamizawa et al. (2004) Cancer Res. 64:3752-3756
31. Yanaihara et al. (2006) Cancer Cell 9:189-198.
32. Johnson et al. (2005) Cell 120:635-647.
33. Lee YS and Dutta A. (2007) Genes Dev. 21:1025-1030.
34. Meng et al. (2007) J. Biol. Chem. 282:8256-8264.
35. Nicolas et al. (2001) J. Biol. Chem. 276:22126-22132.
36. Tapias et al. (2005) Biochim. Biophys. Acta 1730:126-136.
37. Wu et al. (2005) J. Biol. Chem. 280-9745-9751.
38. Lewis et al. (2005) Cell 120:15-20.
39. Krek et al. (2005) Nat. Genet. 37:495-500.
40. Brennecke et al. (2005) PloS. Biol. 3:e85
41. John et al. (2004) PloS. Biol. 3:e363
42. Chintharlapalli et al. (2007) Cancer Res. (in press).
43. Chintharlapalli et al. (2007) Mol. Cancer. Therap. 6:1588-1598.
44. Wacheck V and Zangemeister-Wittke U. (2006) Crit. Rev. Oncol. Hematol. 59:65-73.
45. Gleave M E and Monia B P (2005) Nat. Rev. Cancer 5:468-479.
46. Stein et al. (1997) Antisense Nucleic Acid Drug Dev. 7:151-157.

Any patents or publications mentioned in this specification are indicative of the levels of those skilled in the art to which the invention pertains. These patents and publications are incorporated by reference herein to the same extent as if each individual publication was incorporated by reference specifically and individually. One skilled in the art will appreciate that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A method for suppressing specificity protein (Sp) activity in a breast cancer cell, comprising:
contacting a miR-27a microRNA in the cell with a microRNA antisense oligonucleotide miR-27a consisting of the sequence shown in SEQ ID NO: 1, thereby increasing expression of ZBTB10 gene effective to induce cell cycle arrest in the cell.

2. The method of claim 1, wherein the microRNA antisense oligonucleotide is modified to further comprise a stabilizing group.

3. The method of claim 2, wherein said stabilizing group is a morpholino group.

4. The method of claim 1, wherein the suppressed Sp protein is Sp1, Sp3 or Sp4 or other Sp/KLF protein.

5. The method of claim 1, wherein the gene effective to induce cell cycle arrest is Myt-1.

6. The method of claim 5, wherein Myt-1 induces arrest in G2/M.

7. A method for inhibiting expression of a microRNA in a breast cancer cell, comprising:
delivering to said breast cancer cell, a antisense microRNA oligonucleotide as-microRNA-a27 consisting of the sequence shown in SEQ ID NO: 1.

8. The method of claim 7, wherein the delivery step comprises combining the antisense microRNA with a cationic lipid effective to target the cell.

9. The method of claim 7, wherein the antisense microRNA oligonucleotide is modified to further comprise a stabilizing group.

10. The method of claim 9, wherein said stabilizing group is a morpholino group.

11. A method of treating breast cancer in a subject, comprising:
administering a pharmacologically effective amount of an antisense microRNA-27a oligonucleotide consisting of the sequence shown in SEQ ID NO: 1 to the subject thereby treating the cancer.

12. The method of claim 11, wherein the antisense microRNA oligonucleotide is modified to further a stabilizing group.

13. The method of claim 12, wherein said stabilizing group is a morpholino group.

14. An antisense microRNA-27a oligonucleotide consisting of the sequence shown in SEQ ID NO: 1.

15. The antisense microRNA-27a oligonucleotide of claim 14, wherein the one or more nucleotides are modified with a stabilizing group.

16. The antisense microRNA-27a oligonucleotide of claim 15, wherein the nucleotide(s) is modified with one or more of a morpholino group, a 2'-O-methyl group or a phosphorothioate derivative.

17. The method of claim 14, wherein one or more nucleotides are modified.

* * * * *

SEQUENCE LISTING

```
<160> NUMBER OF SEQ ID NOS: 22

<210> SEQ ID NO 1
<211> LENGTH: 21
<212> TYPE: RNA
<213> ORGANISM: artificial sequence
<220> FEATURE:
<223> OTHER INFORMATION: antisense microRNA-27a oligonucleotide sequence
```

```
<400> SEQUENCE: 1
ccacaccaag ucguguucau u                                              21

<210> SEQ ID NO 2
<211> LENGTH: 21
<212> TYPE: RNA
<213> ORGANISM: artificial sequence
<220> FEATURE:
<223> OTHER INFORMATION: antisense microRNA-27a oligonucleotide sequence

<400> SEQUENCE: 2
ugaacacgac uuggugugguu u                                             21

<210> SEQ ID NO 3
<211> LENGTH: 22
<212> TYPE: DNA
<213> ORGANISM: artificial sequence
<220> FEATURE:
<223> OTHER INFORMATION: sense primer for specificity protein Sp1 cDNA

<400> SEQUENCE: 3
atgggggcaa tggtaatggt gg                                             22

<210> SEQ ID NO 4
<211> LENGTH: 23
<212> TYPE: DNA
<213> ORGANISM: artificial sequence
<220> FEATURE:
<223> OTHER INFORMATION: antisense primer for specificity protein Sp1
      cDNA

<400> SEQUENCE: 4
tcagaacttg ctggttctgt aag                                            23

<210> SEQ ID NO 5
<211> LENGTH: 22
<212> TYPE: DNA
<213> ORGANISM: artificial sequence
<220> FEATURE:
<223> OTHER INFORMATION: sense primer for specificity protein Sp3 cDNA

<400> SEQUENCE: 5
atgactgcag gcattaatgc cg                                             22

<210> SEQ ID NO 6
<211> LENGTH: 22
<212> TYPE: DNA
<213> ORGANISM: artificial sequence
<220> FEATURE:
<223> OTHER INFORMATION: antisense primer for specificity protein Sp3
      cDNA

<400> SEQUENCE: 6
tgtctcttca gaaacaggcg ac                                             22

<210> SEQ ID NO 7
<211> LENGTH: 23
<212> TYPE: DNA
<213> ORGANISM: artificial sequence
<220> FEATURE:
<223> OTHER INFORMATION: sense primer for specificity protein Sp4 cDNA

<400> SEQUENCE: 7
atggctacag aaggagggaa aac                                            23
```

<210> SEQ ID NO 8
<211> LENGTH: 23
<212> TYPE: DNA
<213> ORGANISM: artificial sequence
<220> FEATURE:
<223> OTHER INFORMATION: antisense primer for specificity protein Sp4
      cDNA

<400> SEQUENCE: 8
ttgaccaggg gtggaagaat tac                                           23

<210> SEQ ID NO 9
<211> LENGTH: 21
<212> TYPE: DNA
<213> ORGANISM: artificial sequence
<220> FEATURE:
<223> OTHER INFORMATION: sense primer for ZBTB10 cDNA

<400> SEQUENCE: 9
gctggatagt agttatgttg c                                             21

<210> SEQ ID NO 10
<211> LENGTH: 22
<212> TYPE: DNA
<213> ORGANISM: artificial sequence
<220> FEATURE:
<223> OTHER INFORMATION: antisense primer for ZBTB10 cDNA

<400> SEQUENCE: 10
ctgagtggtt tgatggacag ag                                            22

<210> SEQ ID NO 11
<211> LENGTH: 21
<212> TYPE: DNA
<213> ORGANISM: artificial sequence
<220> FEATURE:
<223> OTHER INFORMATION: sense primer for VEGF cDNA

<400> SEQUENCE: 11
ccatgaactt tctgctgtct t                                             21

<210> SEQ ID NO 12
<211> LENGTH: 20
<212> TYPE: DNA
<213> ORGANISM: artificial sequence
<220> FEATURE:
<223> OTHER INFORMATION: antisense primer for VEGF cDNA

<400> SEQUENCE: 12
atcgcatcag gggcacacag                                               20

<210> SEQ ID NO 13
<211> LENGTH: 24
<212> TYPE: DNA
<213> ORGANISM: artificial sequence
<220> FEATURE:
<223> OTHER INFORMATION: sense primer for VEGFR1 cDNA

<400> SEQUENCE: 13
atggagcgta agaaagaaaa aatg                                          24

<210> SEQ ID NO 14
<211> LENGTH: 23
<212> TYPE: DNA
<213> ORGANISM: artificial sequence
<220> FEATURE:
<223> OTHER INFORMATION: antisense primer for VEGFR1 cDNA -continued

```
<400> SEQUENCE: 14
tcaagtacct ccttttctca cat                                          23

<210> SEQ ID NO 15
<211> LENGTH: 21
<212> TYPE: DNA
<213> ORGANISM: artificial sequence
<220> FEATURE:
<223> OTHER INFORMATION: sense primer for survivin cDNA

<400> SEQUENCE: 15
atggccgagg ctggcttcat c                                            21

<210> SEQ ID NO 16
<211> LENGTH: 21
<212> TYPE: DNA
<213> ORGANISM: artificial sequence
<220> FEATURE:
<223> OTHER INFORMATION: antisense primer for survivin cDNA

<400> SEQUENCE: 16
acggcgcact ttcttcgcag t                                            21

<210> SEQ ID NO 17
<211> LENGTH: 22
<212> TYPE: DNA
<213> ORGANISM: artificial sequence
<220> FEATURE:
<223> OTHER INFORMATION: sense primer for GADPH cDNA

<400> SEQUENCE: 17
acggatttgg tcgtattggg cg                                           22

<210> SEQ ID NO 18
<211> LENGTH: 20
<212> TYPE: DNA
<213> ORGANISM: artificial sequence
<220> FEATURE:
<223> OTHER INFORMATION: antisense primer for GADPH cDNA

<400> SEQUENCE: 18
ctcctggaag atggtgatgg                                              20

<210> SEQ ID NO 19
<211> LENGTH: 23
<212> TYPE: DNA
<213> ORGANISM: artificial sequence
<220> FEATURE:
<223> OTHER INFORMATION: sense primer for Myt-1 cDNA

<400> SEQUENCE: 19
ccttccaaga gtagctccaa ttc                                          23

<210> SEQ ID NO 20
<211> LENGTH: 19
<212> TYPE: DNA
<213> ORGANISM: artificial sequence
<220> FEATURE:
<223> OTHER INFORMATION: antisense primer for Myt-1 cDNA

<400> SEQUENCE: 20
gccggtagct cccatatgg                                               19
```

```
<210> SEQ ID NO 21
<211> LENGTH: 21
<212> TYPE: DNA
<213> ORGANISM: artificial sequence
<220> FEATURE:
<223> OTHER INFORMATION: sense primer for TATA-binding protein cDNA

<400> SEQUENCE: 21
tgcacaggag ccaagagtga a                                        21

<210> SEQ ID NO 22
<211> LENGTH: 20
<212> TYPE: DNA
<213> ORGANISM: artificial sequence
<220> FEATURE:
<223> OTHER INFORMATION: sense primer for TATA-binding protein cDNA

<400> SEQUENCE: 22
cacatcacag ctcccacca                                           20
```